US011633560B2

(12) United States Patent
Hanafialamdari et al.

(10) Patent No.: US 11,633,560 B2
(45) Date of Patent: Apr. 25, 2023

(54) METHOD AND APPARATUS FOR CONTINUOUS MANAGEMENT OF AIRWAY PRESSURE FOR DETECTION AND/OR PREDICTION OF RESPIRATORY FAILURE

(71) Applicant: NovaResp Technologies Inc., Halifax (CA)

(72) Inventors: Hamed Hanafialamdari, Halifax (CA); Klaus Michael Schmidt, Halifax (CA)

(73) Assignee: NovaResp Technologies Inc., Halifax (CA)

( * ) Notice: Subject to any disclaimer, the term of this patent is extended or adjusted under 35 U.S.C. 154(b) by 53 days.

(21) Appl. No.: 17/292,667

(22) PCT Filed: Nov. 11, 2019

(86) PCT No.: PCT/CA2019/051604
§ 371 (c)(1),
(2) Date: May 10, 2021

(87) PCT Pub. No.: WO2020/093177
PCT Pub. Date: May 14, 2020

(65) Prior Publication Data
US 2022/0023561 A1    Jan. 27, 2022

Related U.S. Application Data

(60) Provisional application No. 62/758,577, filed on Nov. 10, 2018.

(51) Int. Cl.
*A61M 16/00* (2006.01)
*G16H 20/40* (2018.01)
*G16H 40/63* (2018.01)

(52) U.S. Cl.
CPC .......... *A61M 16/026* (2017.08); *G16H 20/40* (2018.01); *G16H 40/63* (2018.01);
(Continued)

(58) Field of Classification Search
CPC ............ A61M 16/026; A61M 2230/08; A61M 2230/46; A61M 16/003; A61M 16/022; A61M 16/024; G16H 20/40; G16H 40/63
See application file for complete search history.

(56) References Cited

U.S. PATENT DOCUMENTS 6,257,234 B1    7/2001 Sun
6,889,691 B2    5/2005 Eklund et al.
(Continued)

FOREIGN PATENT DOCUMENTS

CA    3118956 A1    5/2020
EP    1844743 A1    10/2007
(Continued)

OTHER PUBLICATIONS

Extended European Search Report dated Jul. 13, 2022 in EP Patent Application No. 19881164.8 (18 pages).
(Continued)

*Primary Examiner* — Margaret M Luarca
(74) *Attorney, Agent, or Firm* — Bereskin & Parr LLP/S.E.N.C.R.L., s.r.l.

(57) ABSTRACT

Various embodiments are described herein for a controller for controlling the operation of a breathing assistance device that provides breathing assistance to a user. The controller comprises a processor that generates a respiratory index value that is determined during a current monitoring time period to detect a respiratory failure, or predict the respiratory failure when at least one PSG signal is measured. The respiratory index value is compared to a threshold to determine if the control signal needs to be updated to reduce or eliminate respiratory failure that the user is currently experiencing or to prevent a predicted respiratory failure from occurring.

32 Claims, 11 Drawing Sheets

(52) U.S. Cl.
CPC ..... *A61M 2230/08* (2013.01); *A61M 2230/43* (2013.01); *A61M 2230/46* (2013.01)

(56) References Cited

U.S. PATENT DOCUMENTS

| | | | |
|---|---|---|---|
| 7,680,537 | B2 | 3/2010 | Stahmann et al. |
| 7,942,824 | B1 | 5/2011 | Kayyali et al. |
| 8,973,578 | B2 | 3/2015 | Dellaca' et al. |
| 9,358,417 | B2 | 6/2016 | Meyer et al. |
| 9,668,673 | B2 | 6/2017 | Gobbi et al. |
| 11,077,282 | B2 | 8/2021 | Kwok |
| 11,229,765 | B2 | 1/2022 | Bayer et al. |
| 2005/0043644 | A1 | 2/2005 | Stahmann et al. |
| 2005/0081847 | A1 | 4/2005 | Lee et al. |
| 2005/0085866 | A1 | 4/2005 | Tehrani |
| 2005/0256420 | A1 | 11/2005 | Norman et al. |
| 2007/0215156 | A1 | 9/2007 | Kwok |
| 2008/0072896 | A1 | 3/2008 | Setzer et al. |
| 2008/0257349 | A1 | 10/2008 | Hedner et al. |
| 2014/0283834 | A1 | 9/2014 | Ahmad et al. |
| 2014/0350426 | A1 | 11/2014 | Lehrman et al. |
| 2014/0371635 | A1 | 12/2014 | Shinar et al. |
| 2015/0119743 | A1 | 4/2015 | Maksym et al. |
| 2015/0320338 | A1* | 11/2015 | Kane ................. A61M 16/026 600/533 |
| 2016/0106341 | A1 | 4/2016 | Adam et al. |
| 2018/0117270 | A1 | 5/2018 | Bassin |
| 2019/0217030 | A1 | 7/2019 | Burgess et al. |
| 2020/0046923 | A1 | 2/2020 | Hanafialamdari |

FOREIGN PATENT DOCUMENTS

| | | |
|---|---|---|
| WO | 00/010634 A1 | 3/2000 |
| WO | 2011/006199 A1 | 1/2011 |
| WO | 2013/067580 A1 | 5/2013 |
| WO | 2015/127377 A8 | 8/2015 |
| WO | 2015/138474 A1 | 9/2015 |
| WO | 2017/136639 A1 | 8/2017 |
| WO | 2018/072036 A1 | 4/2018 |
| WO | 2019/030632 A1 | 2/2019 |

OTHER PUBLICATIONS

Abdeyrim et al., "What can impulse oscillometry and pulmonary function testing tell US about obstructive sleep apnea: a case-control observational study?", Sleep Breath, Mar. 2016, 20(1): 61-68.

Czövek et al., "Tidal changes in respiratory resistance are sensitive indicators of airway obstruction in children", Thorax, 2016, 71(10): 907-915.

International Search Report and Written Opinion dated Feb. 5, 2020 in International Patent Application No. PCT/CA2019/051604 (10 pages).

International Search Report and Written Opinion dated Jan. 4, 2018 in International Patent Application No. PCT/CA2017/051258 (11 pages).

Mochizuki et al., "Forced Oscillation Technique and Childhood Asthma", Allergology International, Sep. 2012, 61(3): 373-383.

Dellacà et al., "Detection of expiratory flow limitation in COPD using the forced oscillation technique", Eur. Respir. J., Feb. 2004, 23(2): 232-240.

Non-Final Office Action and Notice of References Cited dated Jan. 28, 2022 in U.S. Appl. No. 16/342,724 (6 pages).

International Search Report and Written Opinion dated May 11, 2021 in International Patent Application No. PCT/CA2021/050257 (8 pages).

Non-final Office Action and Notice of References Cited dated Jul. 22, 2022 in U.S. Appl. No. 17/726,719 (8 pages).

Notice of Allowance dated Nov. 15, 2022, issued for U.S. Appl. No. 17/726,719 (14 pages).

* cited by examiner

METHOD AND APPARATUS FOR CONTINUOUS MANAGEMENT OF AIRWAY PRESSURE FOR DETECTION AND/OR PREDICTION OF RESPIRATORY FAILURE

CROSS-REFERENCE

This application is a 35 USC § 371 national stage entry of International Patent Application No. PCT/CA2019/051604, filed Nov. 11, 2019, which claims the benefit of U.S. Provisional Patent Application No. 62/758,577, filed Nov. 10, 2018, and the entire contents of each of which are hereby incorporated by reference.

FIELD

Various embodiments are described herein for an apparatus and method that may be used to operate a breathing device to provide breathing assistance to a user of the breathing device through detection and/or prediction of respiratory failure and other respiratory related features.

BACKGROUND

Individuals suffering acute or chronic respiratory (COPD, asthma, ARDS) or respiratory-related conditions (e.g. sleep apnea) may require assistive devices to maintain respiratory functions at normal levels. Assistive devices such as mechanical ventilators, Positive Airway Pressure (PAP) devices or Continuous Positive Airway Pressure (CPAP) devices are common to provide breathing assistance. However, while such assistive devices are critical with respect to maintaining normal respiratory functions, these devices may also cause harm and distress to a user as a result of the stress or strain due to the amount of pressure or flow imparted on the user's respiratory system. Moreover, all devices are currently retroactive and not proactive to predict and prevent respiratory distress or discomfort. As such, there is a desire for methods and systems to identify and minimize user harm.

It is known in the art that there are various levels of mechanical support for different sorts of respiratory failure. In the most basic form the inspired concentration of oxygen may be increased to percentages above 21% which is the normal atmospheric content of oxygen. This helps a patient in need to satisfy the metabolic need of oxygen for their body. The next higher level of ventilatory support addresses the problem of when the oxygen content of the inhaled gas mixture is not sufficient to keep the homeostasis of the patient's body. This means that also retention of $CO_2$ is becoming a problem. For these sorts of respiratory failure a more invasive way of ventilation including active elevation of the airway pressure above the atmospheric pressure is involved to eliminate $CO_2$ as the end product of the metabolism of the body. As this involves a tightly fitting mask, there are limits to the pressure that can be applied to the system. If elevation of inhaled oxygen and increase of airway pressure facilitated by the mask is no longer sufficient so called mechanical ventilation using an intratracheal tightly fitted tube and/or tracheostomy along with a ventilator is used for ventilation. The parameters that are controlled with a ventilator include the volume of each breath applied to the patient, the respiratory rate per minute which, when taken together, allow for the volume of ventilation of the patient to be controlled long certain time intervals, e.g. every minute. In addition, typically mechanical ventilation also controls for the fraction of inhaled oxygen from 21% to 100% in air and the inspiratory to expiratory ratio of the breathing cycle. If these measures are not sufficient to keep blood oxygen and $CO_2$ levels within safe physiological limits then opposed end expiratory pressure (PEEP) and I/E inspiratory to expiratory ratio is applied. As far as monitoring of ventilation is concerned there are a variety of methods known in the art that include end tidal $CO_2$, inspired $CO_2$, inspired $O_2$, expired $O_2$, blood gas analysis of arterial blood pressure/volume diagrams and volumetric measures of the inspired and expired volumes of ventilation in the patient.

In a sleep apnea the "gold standard" diagnostic test for Obstructive Sleep Apnea (OSA) is polysomnography (PSG), in which respiratory, cardiac, muscular, and neurological parameters are monitored during sleep. The monitoring of these various physiological and neurological parameters allow for the evaluation of oxygen saturation of the blood, pauses of ventilation, EEG activity for determination of sleep phase, and EMG for determination of spontaneous muscular activity.

SUMMARY OF VARIOUS EMBODIMENTS

In a broad aspect, in accordance with the teachings herein, there is provided a controller for controlling the operation of a breathing assistance device that provides breathing assistance to a user, wherein the controller comprises: an input for receiving sensor data to measure at least one airflow parameter of the user's airflow and optionally one Polysomnography (PSG) data to measure at least one PSG parameter; and a processor that is electronically coupled to the input to receive the sensor data and optionally the PSG data, the processor being configured to perform the measurements and to generate a control signal for the breathing assistance device for a current monitoring time period by: generating a respiratory index value that is determined during the current monitoring time period to predict the respiratory failure for the user by: determining a current weighted respiratory status value based on weighting a reactance and a resistance for the user's respiratory system determined from the measured airflow parameters for the current monitoring time period to generate a first index value; generating a second index value that is determined from at least one PSG signal for the current monitoring time period; and generating the respiratory index value from the first and second index values or determining the respiratory index value based on a relative power spectral density between a current time period and a baseline period for a physiological respiratory signal; and updating the control signal when the comparison of the respiratory index value to a threshold value indicates that the respiratory failure is detected or is predicted to occur and otherwise maintaining the control signal at a previous setting.

In at least one embodiment, the processor is electronically coupled to at least one polysomnography (PSG) sensor that measures the at least one PSG signal from the user.

In at least one embodiment, the at least one PSG comprises at least one of EEG, EOG, EMG, respiratory $CO_2$, $O_2$ and/or some other gas in the user's expired breath measured from the user.

In at least one embodiment, the physiological respiratory signal is one of: a flow rate of the air provided to the user, a pressure of the air provided to the user, a tidal volume of air inspired by the user, a resistance of the user's respiratory system.

In at least one embodiment, the physiological respiratory signal is flow rate for the air provided to the user and the relative power spectral density is determined for a frequency range less than about 0.2 Hz or greater than about 2 Hz.

In at least one embodiment, the physiological respiratory signal is a pressure for the air provided to the user and the relative power spectral density is determined for a frequency range less than about 0.2 Hz or greater than about 2 Hz.

In at least one embodiment, the physiological respiratory signal is a tidal volume of air inspired by the user and the relative power spectral density is determined for a frequency range of about 0 Hz to 0.9 Hz.

In at least one embodiment, the physiological respiratory signal is a resistance of the user's respiratory system and the relative power spectral density is determined for a frequency range greater than about 0.4 Hz and preferably 0.5 Hz.

In at least one embodiment, the physiological respiratory signal is a reactance of the user's respiratory system and the relative power spectral density is determined for a frequency range of about 0.3 Hz to 0.6 Hz.

In at least one embodiment, the physiological respiratory signal is an impedance of the user's respiratory system and the relative power spectral density is determined for a frequency of about 0.4 Hz.

In at least one embodiment, the current time period ranges from about 0.1 to 120 seconds and more preferably from about 0.1 to 60 seconds, and the baseline period ranges from about 120 to 300 seconds before a respiratory failure event.

In another broad aspect, in accordance with the teachings herein, there is provided a controller for controlling the operation of a breathing assistance device that provides breathing assistance to a user, wherein the controller comprises: an input for receiving sensor data to measure at least one airflow parameter of the user's airflow; and a processor that is electronically coupled to the input to receive the sensor data and optionally the PSG data, the processor being configured to perform the measurements and to generate a control signal for the breathing assistance device for a current monitoring time period by: generating a respiratory index value that is determined during the current monitoring time period to predict the respiratory failure for the user by: performing a Forced Oscillation Technique (FOT) on the user to determine at least one of a reactance, resistance and an impedance of the user's respiratory system; and generate the respiratory index value based on a relative power spectral density between a current time period and a baseline period for a physiological respiratory signal including at least one of the reactance, resistance and an impedance of the user's respiratory system; and updating the control signal when the comparison of the respiratory index value to a threshold value indicates that the respiratory failure is detected or is predicted to occur and otherwise maintaining the control signal at a previous setting.

In another broad aspect, in accordance with the teachings herein, there is provided a method of for adjusting an airflow provided by a breathing assistance device to a user, wherein the method comprises: receiving sensor data for measuring airflow parameters of the airflow and optionally additionally receiving Polysomnography (PSG) data for measuring at least one PSG signal; operating a processor that is configured to electronically receive the data to perform the measurements and to generate a control signal for the breathing assistance device for a current monitoring time period by: generating a respiratory index value that is determined during the current monitoring time period to predict the respiratory failure, for the user by: determining a current weighted respiratory status value based on a weighting a reactance and a resistance for the user's respiratory system determined from the measured airflow parameters for the current monitoring time period to generate a first index value; generating a second index value that is determined from the at least one PSG signal; and generating the respiratory index value from the first and second index values; or determining the respiratory index value based on a relative power spectral density between a current time period and a baseline period for a physiological respiratory signal; updating the control signal when the comparison of the respiratory index to a threshold value indicates that the respiratory failure is predicted to occur and otherwise maintaining the control signal at a previous setting; and sending the control signal to the breathing assistance device to adjust the operation of the breathing assistance device during use.

In at least one embodiment, wherein an actuator is used to generate an airway pressure perturbation that is superimposed on the airflow that is provided to the user and the airway pressure perturbation is generated to have at least one frequency.

In at least one embodiment, the at least one frequency is in the range of 0.001 Hz to 100 THz.

In at least one embodiment, the at least one frequency is at about 37 Hz or at about 79 Hz the airway pressure perturbation is about 0.1 cmH2O.

In at least one embodiment, the measured signals are preprocessed before being processed by the processor, the preprocessing comprising amplification and filtering.

In another broad aspect, in accordance with the teachings herein, there is provided a method of for adjusting an airflow provided by a breathing assistance device to a user, wherein the method comprises: receiving sensor data for measuring airflow parameters of the airflow; operating a processor that is configured to electronically receive the data to perform the measurements and to generate a control signal for the breathing assistance device for a current monitoring time period by: generating a respiratory index value that is determined during the current monitoring time period to predict the respiratory failure for the user by: performing a Forced Oscillation Technique (FOT) on the user to determine at least one of a reactance, resistance and an impedance of the user's respiratory system; and generating the respiratory index value based on a relative power spectral density between a current time period and a baseline period for a physiological respiratory signal including at least one of the reactance, resistance and an impedance of the user's respiratory system;

and updating the control signal when the comparison of the respiratory index to a threshold value indicates that the respiratory failure is predicted to occur and otherwise maintaining the control signal at a previous setting; and sending the control signal to the breathing assistance device to adjust the operation of the breathing assistance device during use.

In another broad aspect, in accordance with the teachings herein, there is provided a controller for controlling the operation of a breathing assistance device that provides breathing assistance to a user, wherein the controller comprises: an input for receiving sensor data to measure at least one airflow parameter of the user's airflow; and a processor that is electronically coupled to the input to receive the sensor data, the processor being configured to perform the measurements and to generate a control signal for the breathing assistance device for a current monitoring time period by: generating a respiratory index value that is determined during the current monitoring time period to detect a respiratory failure for the user by: determining a current weighted respiratory status value based on weighting a reactance and a resistance for the user's respiratory system determined from the measured airflow parameters for the current monitoring time period; and generating the respiratory index value based on a deviation of the current weighted respiratory status value from a baseline weighted respiratory status value; and updating the control signal when the comparison of the respiratory index value to a threshold value indicates that the respiratory failure is detected to occur and otherwise maintaining the control signal at a previous setting.

In at least one embodiment, the sensor data to measure at least one airflow parameter of the user's airflow is based on at least one of pressure and airflow rate of air provided to the user from the breathing assistance device.

In at least one embodiment, the baseline weighted respiratory status value is determined during from measurements obtained from the user during an initial monitoring period when the user first starts using the breathing assistance device or during a healthy breathing period without any respiratory failure events when the user is using the breathing assistance device.

In at least one embodiment, the baseline weighted respiratory status value is updated periodically from measurements obtained from the user based on a recent monitoring period while the user is using the breathing assistance device.

In at least one embodiment, the user has a chronic respiratory condition the baseline weighted respiratory status value is determined from a population of individuals having a same physical size, age, gender and the chronic respiratory condition compared to the user.

In at least one embodiment, when the user has a chronic respiratory condition the baseline weighted respiratory status values is determined from measurements obtained from the user when the user is breathing normally after receiving treatment for the chronic respiratory condition.

In at least one embodiment, values for the weights are determined from values in a table of weights that are categorized based on different respiratory conditions and different levels of severity for the respiratory condition for different patient populations.

In at least one embodiment, a first weight applied to a reactance value relative is larger or smaller compared to a second weight applied to a resistance value depending on whether the user has a respiratory condition and a severity level of the respiratory condition.

In at least one embodiment, the current weighted respiratory status value and the baseline weighted respiratory status value are impedance values.

In at least one embodiment, the controller comprises an actuator that is electrically coupled to and controlled by the processor to generate an airway pressure perturbation that is superimposed on the airflow that is provided to the user.

In at least one embodiment, the breathing assistance device comprises the actuator or the breathing assistance device controller comprises the actuator.

In at least one embodiment, the airway pressure perturbation is generated to have at least one frequency for FOT measurement.

In at least one embodiment, the controller has a housing with a first end that is releasably coupled to the breathing assistance device via a first airflow pathway and a second end that is releasably coupled by a second airflow pathway to an entry element that is used by the user to receive the breathing assistance.

In another broad aspect, in accordance with the teachings herein, there is provided a method of for adjusting an airflow provided by a breathing assistance device to a user, wherein the method comprises: receiving data for measuring airflow parameters of the airflow; operating a processor that is electronically configured to receive the data to perform the measurements and to generate a control signal for the breathing assistance device for a current monitoring time period by: generating a respiratory index value that is determined during the current monitoring time period to detect a respiratory failure for the user by: determining a current weighted respiratory status value based on a weighting a reactance and a resistance for the user's respiratory system determined from the measured airflow parameters for the current monitoring time period; and generating the respiratory index value based on a deviation of the current weighted respiratory status value from a baseline weighted respiratory status value; updating the control signal when the comparison of the respiratory index to a threshold value indicates that the respiratory failure is detected to occur and otherwise maintaining the control signal at a previous setting; and sending the control signal to the breathing assistance device to adjust the operation of the breathing assistance device during use.

In another broad aspect, in accordance with the teachings herein, there is provided a system for providing breathing assistance to a user, wherein the system comprises: a breathing assistance device that generates an airflow comprising at least one pressure impulse or a continuous pressure flow rate; an entry element that is coupled to the breathing assistance device and is worn by the user to provide the airflow to the user during use; and a breathing assistance device controller that is defined according to any of the applicable teachings herein.

In at least one embodiment, the breathing assistance device is any type of invasive or a Non-Invasive Ventilation (NIV) device comprising an anesthesia machine, an oxygenator of COPD, an ICU ventilator, a home ventilator, a mechanical ventilator, a continuous positive airway pressure (CPAP) device, a BiPAP device, an APAP device and a PAP device.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

Figure 1:
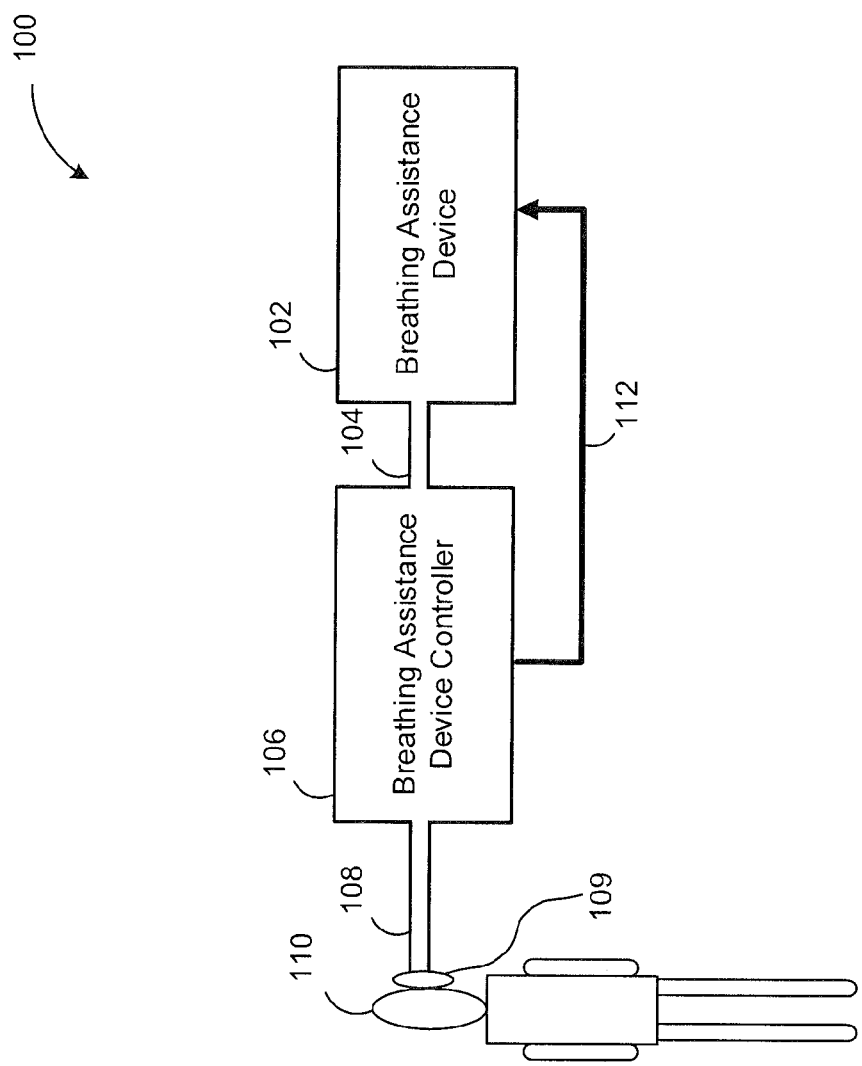
FIG. 1 is a block diagram of an example embodiment of a breathing assistance system for controlling or tuning a breathing assistance device during use by a user based on detection and/or prediction of respiratory failure in accordance with the teachings herein.

Further aspects and features of the example embodiments described herein will appear from the following description taken together with the accompanying drawings.

DETAILED DESCRIPTION OF THE EMBODIMENTS

Various embodiments in accordance with the teachings herein will be described below to provide an example of at least one embodiment of the claimed subject matter. No embodiment described herein limits any claimed subject matter. The claimed subject matter is not limited to devices or methods having all of the features of any one of the devices or methods described below or to features common to multiple or all of the devices and or methods described herein. It is possible that there may be a device or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical, fluidic or electrical connotation. For example, as used herein, the terms coupled or coupling can indicate that two elements or devices can be directly connected to one another or connected to one another through one or more intermediate elements or devices via an electric signal, an electrical connection, a mechanical element, a fluid or a fluid transport pathway, for example, depending on the particular context.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term such as, but not limited to, 1%, 2%, 5% or 10%, if this deviation would not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as, but not limited to, 1%, 2%, 5% or 10%, for example.

The example embodiments of the devices, systems or methods described in accordance with the teachings herein may be implemented as a combination of hardware and software. For example, the embodiments described herein may be implemented, at least in part, by using one or more computer programs, executing on one or more programmable devices comprising at least one processing element and at least one storage element (i.e. at least one volatile memory element and at least one non-volatile memory element). The hardware may comprise one or more input devices including at least one of a touch screen, a keyboard, a mouse, buttons, keys, sliders and the like, as well as one or more output devices including at least one of a display, a speaker, a printer, and the like depending on the implementation of the hardware.

It should be noted that the term "user" covers a person who is using a breathing assistance device. In some cases, the user may be an individual that is using the breathing assistance device in their home or a non-medical setting. In other cases, the user may be a patient who is using the breathing assistance device in a medical setting such as a clinic or a hospital, for example.

Oscillometry, also known as the forced oscillation technique (FOT), may be performed within the field of respiratory diagnostics by superimposing fluctuations on airway pressure while a user is breathing normally and measuring the resultant pressure and flow rate to determine the mechanical properties of the user's respiratory system. For example, the measured pressure and flow rate may then be used to determine the mechanical impedance of the respiratory system. This mechanical impedance is the ratio of the oscillatory pressure to the flow rate in the frequency domain, which can be expressed as a complex quantity as a function of frequency. More specifically, the real part of the mechanical impedance may be regarded as the respiratory system resistance ($R_{rs}$) and the imaginary part can be regarded as the respiratory system reactance ($X_{rs}$).

When the complex mechanical impedance of the respiratory system is described, it is generally common to present the average $R_{rs}$ and average $X_{rs}$ behavior over a frequency range of interest. These average values can normally be computed from averaging impedance values estimated using frequency domain methods such as by performing Fourier transforms on the measured pressure and flow values taken from multiple finite overlapping time windows, or from averaging over a time course computed from recursive time domain methods that can also effectively examine short duration overlapping time periods.

However, the inventors have determined temporal variations that occur in $R_{rs}$ and in $X_{rs}$ during respiration may contain information related to an individual's breathing and their respiratory system. The temporal variations for $R_{rs}$ and the $X_{rs}$, which can be denoted as $R_{var}$ and $X_{var}$ respectively, can be determined using a frequency domain technique such as the short-time-Fourier transform (STFT) or the Wavelet transform. Although it has been established that variations in the amplitude of $X_{var}$ between inspiration and expiration contains signs of respiratory health, the inventors have determined that there is a linkage between the $R_{var}$ and the $X_{var}$ when they are being determined using FOT and $R_{var}$ and $X_{var}$ are changing over time.

For example, it is known that variations in resistance are increased in asthmatic patients and that variations in reactance increase in COPD patients. However, the inventors have discovered that some of these variations in reactance for COPD patients leak into variations in resistance and the inventors have also discovered that both of these should both be taken into account for accurate diagnosis and monitoring. The inventors have found that the same situation occurs with asthmatic patients where variations in reactance leak into variations in resistance and both the reactance and the resistance need to be included in diagnosis and decision making for effective treatment.

Therefore, conventional technologies that monitor $R_{rs}$ and $X_{rs}$ separately may be missing essential information about the health of the individual's lungs. However, in accordance with the teachings herein, $R_{var}$ and $X_{var}$ are monitored and the linkage between $R_{var}$ and the $X_{var}$ may be used to determine certain situations such as when a person, for whom the $R_{var}$ and the $X_{var}$ are determined, is experiencing respiratory failure. This has not been previously determined by others in this field.

A respiratory failure may be understood to cover all diseases and conditions which can result in a negative change in a person or animal's respiratory system such as a breathing obstruction or small airways. In some cases, the respiratory failure may be a temporary respiratory event that occurs such as during OSA or an asthma attack or it may be due to a chronic respiratory condition such as lung cancer, cystic fibrosis or chronic obstructive pulmonary disease.

In accordance with one aspect of the teachings herein, the inventors have determined that the link or relationship between $R_{var}$ and the $X_{var}$ can be used to determine a respiratory index that is used to detect when respiratory failure is occurring and in such cases to take corrective actions to help the individual to breathe more normally again. The actions may include, but are not limited to, various techniques that are applied to keep the user's airway open to avoid hypo-oxygenation or hypocapnia in the user's blood. For example, for a COPD patient, when the combination of $X_{var}$ and $R_{var}$ shows a respiratory failure the breathing assistance device needs to adjust its inspiratory and expiratory pressures. In addition, the breathing assistance device may change the mixture of gases provided to the patient (e.g. in COPD there may be a change in the concentration of oxygen provided to the patient) to also help with that specific disease. The index may be a combination of $R_{var}$ and $X_{var}$. Conventionally, this has never been done and advantageously this may be used to improve the respiratory health status of the individual in a short period of time.

The link or relationship between $R_{var}$ and $X_{var}$ can be determined using a benchtop lung simulator made using physical elements an example of which is described in U.S. provisional patent application No. 62/758,394 entitled "BENCHTOP WITHIN-BREATH DYNAMIC LUNG SIMULATOR" and filed on Fri, Nov. 9, 2018 and in U.S. non-provisional patent application No. 16/678,153 entitled "BENCHTOP WITHIN-BREATH DYNAMIC LUNG SIMULATOR" and filed on Fri, Nov. 8, 2019, the entirety of which is hereby incorporated by reference.

Figure 6:
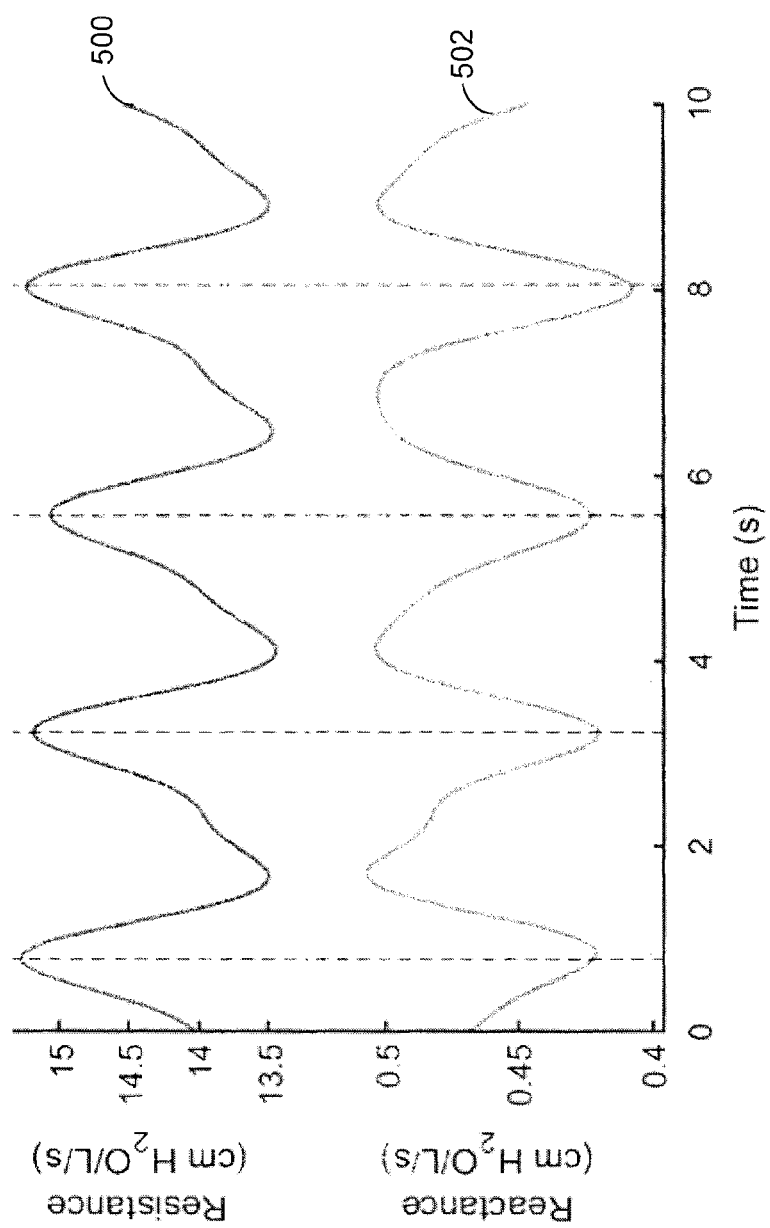
FIG. 6 shows example waveforms for resistance and reactance.

For example, FIG. 6 shows an example of a resistance ($R_{var}$) waveform 500 and a reactance ($X_{var}$) waveform 502 which were obtained performing FOT on a benchtop lung simulator (described in the above-noted US Provisional application) using a perturbation frequency of 20 Hz. While the resistance is only being changed on the benchtop lung simulator the measurements show that the reactance is also varying. This leakage is important because it can help diagnose and monitor the health of the lung better.

Figure 7:
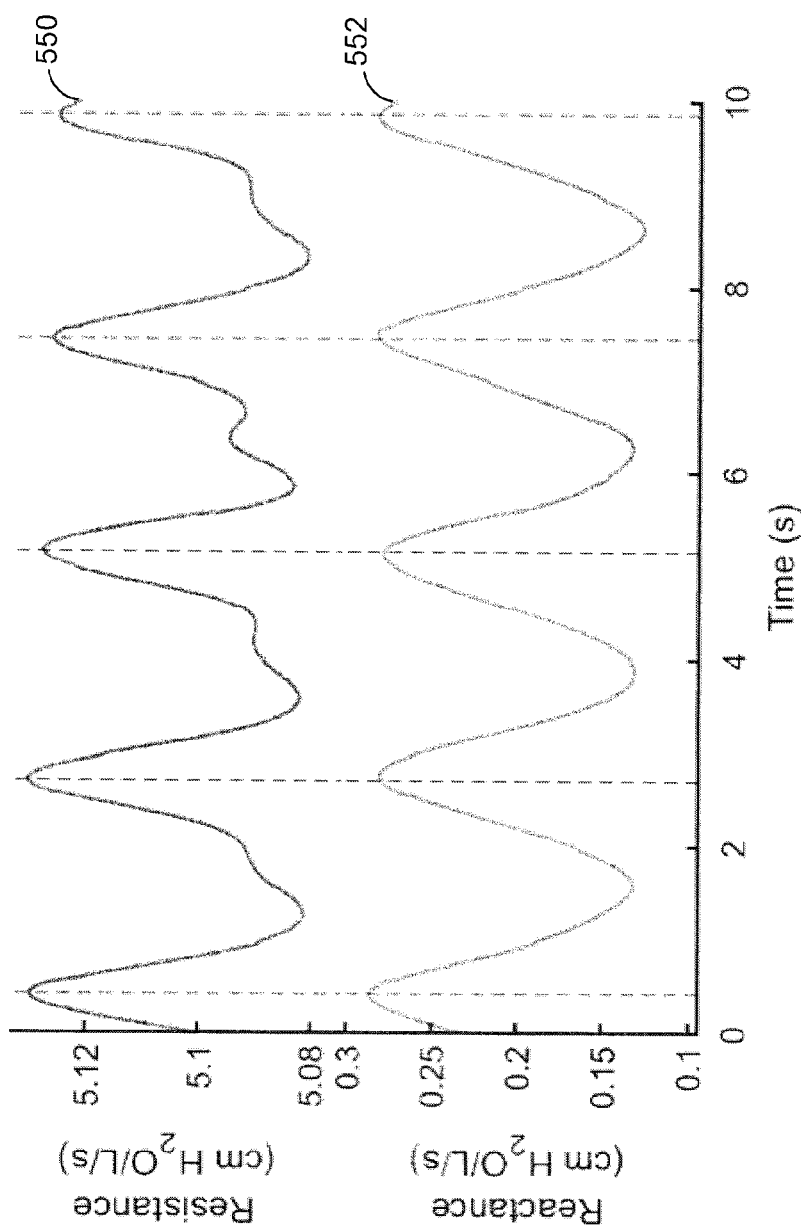
FIG. 7 shows another example of waveforms for resistance and reactance.

In another example, FIG. 7 shows a resistance ($R_{var}$) waveform 550 and a reactance ($X_{var}$) waveform 552 that was also obtained using FOT on a benchtop lung simulator (described in the above-noted US Provisional application) with a perturbation frequency of 20 Hz. While the reactance is only being changed on the bench-top lung simulator, there is a leakage in resistance at the same frequency which not only generates variations in resistance that are measured by FOT, but also increases the mean resistance that is measured when the reactance is not varying.

In accordance with another aspect of the teachings herein, the inventors have determined that the link or relationship between $R_{var}$ and the $X_{var}$ can be used along with the measurement of certain physiological and/or neurological parameters to determine a respiratory index that can be used to predict when respiratory failure will occur and in such cases to take corrective actions to reduce the chances that the individual will experience the respiratory failure that was predicted. For example, the changes in $R_{var}$ and $X_{var}$, and therefore the change in $Z_{var}$, and their weighted versions $R_{var,w}$, $X_{var,w}$ and $Z_{var,w}$, can be correlated with a physiological measurement (e.g. CO2) and/or a neurological measurement (e.g. EEG) to predict when respiratory failure will happen. However, in this case, the corrective actions are proactive to avoid respiratory failure which is in contrast with the respiratory detection technique described previously which is reactive in nature since corrective action is only taken after the individual starts experiencing respiratory failure. Conventionally, proactive corrective actions based on prediction has never been done and advantageously this may be used so that the individual's respiratory health status does not worsen and/or stays within acceptable limits.

In accordance with another aspect of the teachings herein, the inventors have determined that the change in certain characteristics of physiological respiratory parameters relative to baseline values obtained when a patient is breathing normally may be used to predict when a respiratory event like sleep apnea or respiratory failure will occur. Examples of these teachings are discussed further with respect to FIGS. 8 to 14.

In either of the aforementioned aspects, depending on the indices that are determined, which are generally numbers, the operating parameters of the breathing assistance device may then be adjusted to ensure that the user of the breathing assistance device experiences minimal respiratory failure. Accordingly, at least one of these indices can be used to generate a feedback control signal that is used to control the operation of the breathing assistance device. These indices may be determined for a given time period during which many numbers are generated which can be collectively referred to as the respiratory index signal. The respiratory index signal can be used to control the breathing assistance device over the given time period.

Therefore, the teachings herein provide for the real time assessment of lung mechanics to detect respiratory failure, or to predict respiratory failure when at least one other physiological signal is measured, based on the determination of a respiratory index and comparison of the respiratory index to a normative values, which may be represented by a threshold in at least some cases. The respiratory index can be continuously determined and used to continuously manage the settings of a breathing assistance device to reduce, mitigate or avoid the respiratory failure.

Previously it was not possible to determine the respiratory failure of the user of a breathing assistance device in an automated fashion. Accordingly, breathing assistance devices were conventionally controlled in a manual fashion by a medical practitioner who set and then adjusted the operational parameters of the breathing assistance device every so often. This was detrimental since if the user started experiencing respiratory failure it was not conventionally possible to automatically adjust the breathing assistance device to reduce the effect or amount of respiratory failure encountered by the user which may be fatal in some situations where response time is critical for adjusting the operation of the breathing assistance device. Furthermore, such conventional techniques will not even allow for the prediction of imminent respiratory failure.

More recently, other techniques including traditional FOT/Oscillometry have been used to automatically adjust the parameters of breathing assistance devices. However, traditional FOT uses averaging and therefore there is a delay of multiple seconds before any detection can happen. This is also detrimental to the user health. Moreover automatic adjusting of breathing assistance devices utilizing techniques such as only sensing the airflow or oxygen levels does not provide enough information of the health of the complete respiratory system.

It is believed that the techniques of determining the indices of a user of a breathing assistance device and generating a control signal to control the breathing assistance device to maintain the respiratory health of the user in a certain range where the user is not experiencing respiratory failure, in accordance with the teachings herein, will increase the rate of adoption of use of breathing assistance devices where the use is voluntary (i.e. as for sleep apnea devices). This method also provides technical advantages such as an increase in the speed of adaptation of the breathing assistance device to any respiratory failure encountered by the user as the methods can detect or predict the respiratory failure relatively quickly and can also take reactive or proactive steps quickly to control the breathing assistance device to reduce the level/amount of respiratory failure that is encountered by the user or prevent the respiratory failure from even happening. This can be critical in some cases where increased respiratory failure can have significant, if not fatal, consequences to the user.

Referring now to FIG. 1, illustrated therein is a block diagram of a breathing assistance system 100 for controlling or tuning a breathing assistance device using the forced oscillation technique based on detection and/or prediction of respiratory failure in accordance with at least one embodiment of the teachings herein. The system 100 comprises a breathing assistance device 102 that generates an airflow that is provided to a user 110 via air transport pathways 104 and 108 and, for example, a laryngeal tube, a breathing mask or an endotracheal tube 109 (hereinafter collectively referred to as an "entry element"). The airflow can be at least one pressure pulse of air, a continuous flow of air, or a superposition of pressure pulses of air and a continuous flow of air. The airflow is controllable by adjusting at least one of the air pressure and flow rate of the breathing assistance device 102 via corresponding input controls on the breathing assistance device 102.

In some embodiments, the breathing assistance device 102 may be a mechanical ventilator for providing breathing support to the user. In other embodiments, the breathing assistance device 102 may be a CPAP, APAP, BiPAP or PAP device for providing breathing support to the user. In other embodiments, the breathing assistance device 102 may be a respiratory treatment delivery device such as, but not limited to, respiratory treatment delivery devices that assist a user in clearing their lungs and coughing out secretions. In other instances the breathing assistance device 102 may be an anesthesia machine in the OR, an ICU ventilator, a home ventilator and oxygenator of COPD, and any other machine that provides breathing assistance to a user who has a respiratory disease. Therefore, in general, the teachings described herein for the detection and/or prediction of respiratory failure and the proactive or reactive actions that are taken to reduce, remove or pre-empt respiratory failure can be used with all types of ventilation including invasive (with tube) and non-invasive (tubeless) ventilation.

A breathing assistance device controller 106 is coupled to the breathing assistance device 102 via the air transport pathway 104 (which may also be called the flow passage 104) and receives airflow from the breathing assistance device 102 and delivers the airflow via the air transport pathway 108 and the entry element 109 to the user 110. It should be noted that the term "air" in the present disclosure is used generally to denote the flow of gas and other particles through the system. For example, the output of a mechanical ventilator may include gasses and/or vapors other than air such as, but not limited to, anesthetics, for example which are typically vapors but can also be gases. In a PAP device, water vapor may be combined with air. In some embodiments of the breathing assistance device, gaseous medication (i.e. steroids, oxygen, Nitrogen, etc.) may be added to the air flow and provided to the patient under ventilation based on respiratory health and/or measured comfort level. For example, the medication may include an appropriate amount of steroids that may be used daily to improve the CPAP experience for the user. The airflow may be delivered to the user 110 via the entry element 109. In the present embodiment, the entry element 109 may be a mask worn over the user's 110 nose and mouth or just over the nose for alternative masks. In other embodiments, the entry element 109 may be an endotracheal tube inserted into the trachea by means of intubation or tracheostomy.

In embodiments in which the breathing device 102 is a mechanical ventilator, there are actually two air pathways (not shown) instead of just the air transport pathway 104 (which may also be called a flow passage) where one of the pathways is used for inhalation and the other of these pathways is used for exhalation. The pathways shown in FIG. 1 apply for the case where the breathing assistance device 102 is a PAP device. It may be thus understood that the breathing assistance device 102 provides at least one pathway to allow air to flow from the air transport pathway 104 to the air transport pathway 108. It may further be understood that there can be embodiments in which the breathing assistance device controller 106 is at least partially or completely incorporated "inline" with the airflow pathways from the breathing assistance device 102 to the user 110.

In the present example embodiment, the breathing assistance device controller 106 comprises one or more sensors (not shown) to measure the various parameters of the airflow being delivered to the user 110. For example, sensors can be attached to the mask worn by the user 110 which may result in ideal SNR for the sensor data obtained from the sensors. Alternatively, the sensors, such as ultrasonic sensors for example, can be attached in the tubing pathway. In either case, these sensors can be used to measure both inspiration and expiration. However, in the case of a PAP machine, such sensors are located close to the mask because the tube 108 only carries an inspiratory flow whereas in a mechanical ventilator the sensors can be attached to the mask or endotracheal tube or they can be located anywhere along the tubes that are used for the inspiratory pathway and the expiratory pathway.

In some embodiments, the breathing assistance device controller 106 may not include these sensors but may instead read these parameters from the breathing assistance device 102 since the breathing assistance device 102 may also be equipped with sensors for measuring airflow parameters. The breathing assistance device controller 106 may further comprise a device to provide a forced oscillation signal, which has changes in air pressure. In some embodiments, a sensor for measuring both air pressure and airflow is present. In other embodiments, dedicated sensors may be used to measure the airflow or the air pressure such that more than one sensor may be used with the breathing assistance device controller 106. For example, some sensor technologies use a laser to detect movement or ultrasound can be used to detect both pressure and flow rate using one sensor (as the measured flow rate can be determined from dividing the measured pressure by a known resistance).

The measured airflow parameters such as air volume, air pressure and airflow may be used by the breathing assistance device controller 106 to generate a control signal 112 that can be used as feedback to adjust the operation of the breathing assistance device 102. For example, the breathing assistance device controller 106 can employ a control method, such as method 300, for example, that performs detection of when respiratory failure is occurring and then generates the control signal to provide a corrective action so that the user no longer experiences the respiratory failure.

Alternatively, in some embodiments, the breathing assistance controller 106 can employ a control method, such as method 500, for example, to predict when respiratory failure will occur (e.g. perhaps up to and including the next few minutes) and to then generate the control signal to provide a proactive action so that the user does not experience the predicted respiratory failure. In such embodiments, additional measured signals can be used to implement the predictive method. For example, the measured signals can be one or more of the physiological or and/or neurological signals that are obtained during polysomnography (PSG) and hereafter referred to as PSG signals. Accordingly, PSG signals include at least one physiological signal and/or at least one neurological signal. Sensors for measuring such signals are not shown in FIG. 1 but such sensors are known by those skilled in the art.

In both of the detection and prediction embodiments, the control signal 112 may be used to adjust one or a few or all of the adjustable parameters of the breathing assistance device 102. For example, parameters that may be adjusted include at least one of the flow rate of the airflow, the volume of the airflow, the pressure of the airflow, the frequency of certain changes in the airflow (like changes in the flow rate, volume, pressure and amplitude of the airflow), the amplitude of the airflow and the phase of the airflow that can be generated by the breathing assistance device 102.

Figure 2:
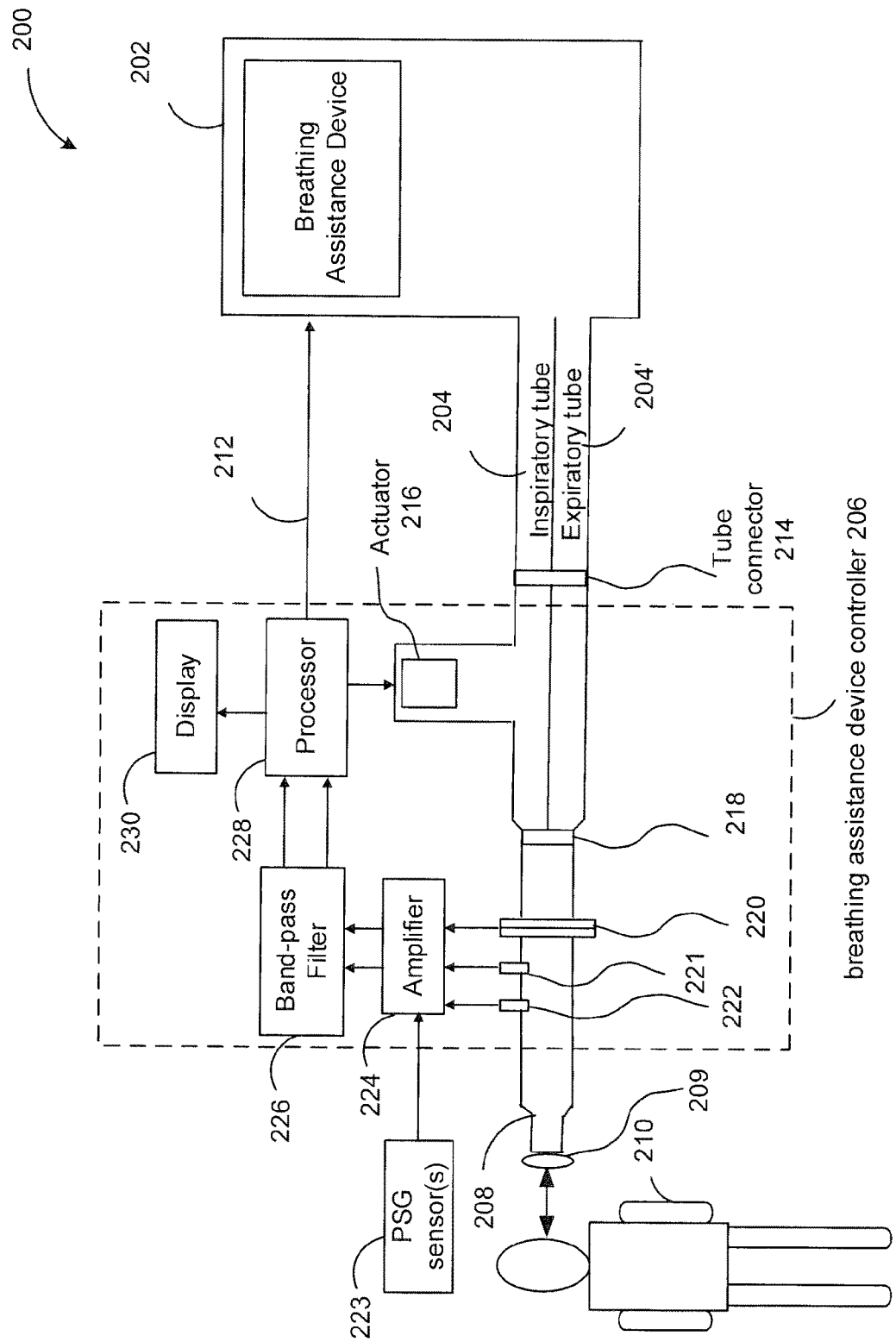
FIG. 2 is a block diagram of another example embodiment of a breathing assistance system for controlling or tuning a breathing assistance device during use by a user based on detection and/or prediction of respiratory failure in accordance with the teachings herein.

Referring now to FIG. 2, shown therein is a block diagram of an example embodiment of a breathing assistance system 200 for controlling or tuning a breathing assistance device 202 during use by a user based on detection and/or prediction of respiratory failure in accordance with the teachings herein. Elements that correspond to those in FIG. 1 have been numbered similarly. Similar to the configuration of the breathing assistance system 100, a breathing assistance device 202 generates airflow that is provided to a user 210 via air transport pathways 204 and 204' and the breathing tube 208 and the airflow is monitored by a breathing assistance device controller 206 for modifying the operation of the breathing assistance device 202 under certain conditions. Similar to FIG. 1, the airflow may be delivered to the user 210 via an entry element 209. In this example embodiment the entry element 209 may be a mask worn over the user's 210 nose and optionally the user's mouth. In other embodiments, the entry element 209 may be an endotracheal tube inserted into the trachea by means of intubation or tracheostomy.

FIG. 2 provides additional details with respect to the various system components that may be employed. In some embodiments, the breathing assistance device 202 may be a mechanical ventilator for providing breathing support. In other embodiments, the breathing assistance device 202 may be a PAP device for providing breathing support. Other options are available for the breathing assistance device 202 as explained for the breathing assistance device 102.

In the present embodiment, the breathing assistance device 202 is a mechanical ventilator and provides an inspiratory tube 204 and an expiratory tube 204' for airflow leaving and returning to the breathing assistance device 202, respectively. The inspiratory tube 204 and the expiratory tube 204' may be connected to the breathing assistance device controller 206 at one airflow pathway using the tube connector 214. The airflow may then flow to the user 210 through another airflow pathway of the breathing assistance device controller 206. The airflow from the inspiratory tube 204 may be subjected to perturbation from a forced oscillation produced by a motor or an actuator (hereinafter referred to as an "actuator" to refer to both cases) 216 generating an oscillation of air at a desired frequency. The actuator may be one of a loud speaker, an electromagnet, a piezoelectric device, a piston and a motor, for example. The choice of actuator may be dependent on the design specifications such as the physical size of the device 206 as well as on the limitations imposed on the Bill of Materials (BOM). It should be noted that in some embodiments, the actuator 216 can be included in the breathing assistance device 202 and not in the breathing assistance device controller 206. Alternatively, in some embodiments, both the breathing assistance device 202 and the breathing assistance device controller 206 can include separate actuators.

The oscillation pressure signal has an oscillation frequency that may be at any frequency that is practical for performing air pressure and airflow measurements. For example, the frequency may include, but is not limited to the range of 0.001 Hz to 100 MHz or even up to 1 THz. In some embodiments, the frequency range is from a lower frequency of 5 Hz, 10 Hz, or 20 Hz to an upper frequency of 100 MHz or 1 THz. In some embodiments, the frequency range is from 40 Hz to an upper frequency of 100 MHz or 1 THz. In some embodiments, the frequency is about 37 Hz or about 79 Hz where harmonics of these frequencies will not interfere with one another during FOT measurement. In some embodiments, a multi-frequency signal can be used having different harmonics. For example, the oscillation signal may be a square wave or a triangular wave. A multi-frequency signal is useful in certain situations such as when for calculating impedance at different frequencies. The oscillation pressure signal is superimposed into the modified and/or spontaneous breathing of the user 210.

In some embodiments, the generated oscillation pressure signal may also be controlled to deliver a desired pressure. In some cases, it may be preferable to produce pressures (i.e. amplitude of the generated oscillation signal) that do not exceed a peak-to-peak value of about 0.01 cm $H_2O$ to about 2 cm $H_2O$. In some other cases, the pressure may be chosen on the basis of the frequency of oscillation or on the sensitivity and precision of the flow rate sensor and/or the pressure sensor. In some cases, the amplitude of the oscillation (i.e. the pressure) may follow an inverse frequency trend (1/f). For example, if frequencies of 6, 11 and 19 Hz are used, the amplitude of pressure at 6 Hz is higher than the amplitude of pressure at 11 Hz. Similarly, the amplitude of pressure at 11 Hz is higher than the amplitude of pressure at 19 Hz.

The inspiratory tube 204 and the expiratory tube 204' may be combined prior to reaching the user 210 at a junction using a tube fitting 218 connected to a breathing tube 208. Subsequent to the tube fitting 218, the combined airflow may be sensed to determine parameters such as the airflow and the air pressure. In this example embodiment, a sensing system is used that comprises a flow transducer 220 and a pressure transducer 221. It should be noted that the flow transducer 220 may also be called a flow rate transducer or an airflow transducer. The sensor type used for the transducers 220 and 221 can be any appropriate transducer device, including but not limited to, ultrasonic, pneumatic and piezoelectric transducers, for example. In some embodiments, the airflow can be measured and calculated by recording the pressure drop across a pneumotachograph, which is used as the sensor.

The outputs of the flow transducer 220 and the pressure transducer 221 may be preconditioned prior to being further processed. For example, the output signals from the transducers 220 and 221 may be amplified by an appropriate amplifier 224 to obtain the desired signal amplitudes. For example, in some embodiments, the amplifier 224 may be a lock-in amplifier which may be used to reduce signal noise to help focus on the frequency of interest. It should be noted that separate amplifiers can be used for each measured signal or a dual channel amplifier may be used.

The amplified signal may then be filtered to remove extraneous frequency domain information. In the present embodiment, a band-pass filter 226 with a tuned center-frequency corresponding to the frequency of the oscillation produced by the actuator 216 may be used. In some embodiments, the passband may be made sufficiently narrow such that a notch filter can be used when a single frequency is used for FOT. The band-pass filter 226 has a narrow passband but it is preferably large enough to contain any side lobes in the measured signals that contains modulated breathing information.

After the signals have been amplified and filtered, the signals are received by the processor 228 for further processing and analysis in order to generate a control signal 212 that is provided to the breathing assistance device 202 to adjust its operation, as described in more detail below. In some embodiments, the processor 228 may a programmable device such as a programmable microcontroller or a field programmable gate array (FPGA). In other embodiments, the processor may be part of a single-board computer system platform such as the Arduino platform, or Raspberry Pi platform. In yet other embodiments, the signal filtering may be performed using the processor 228 such as by using digital signal processing (DSP) techniques such that separate filtering device 226 may not be necessary.

The control signal 212 can be provided to the breathing assistance device 202 using any method known to those skilled in the art. For example, the control signal 212 can be provided through a wired connection. However, in other implementations, the control signal may be communicated wirelessly to the breathing assistance device 202. The measured airflow parameters and control signal may also be shown on an optional display 230 provided on the breathing assistance device controller 206.

The breathing assistance device controller 206 can be configured to operate continuously to monitor the pressure and flowrate of the airflow provided to the user 210 to allow for constant adjustment of the operation of the breathing assistance device 202. Doing so may permit real-time or near real-time adaptive adjustments to be made to minimize any respiratory failure that is experienced by the user 210. In other embodiments, the breathing assistance device controller 206 may alternatively be controlled to operate intermittently, for example, at a set time interval such as every 30 seconds or every 60 seconds. Such operating conditions may be preferred if the breathing assistance device controller 206 is battery operated so as to help extend the operational lifetime of the breathing assistance device 202.

In embodiments in which the system 200 is used to predict when the user will soon experience respiratory failure, the sensing system also includes at least two additional sensors including a gas sensor 222 and one or more sensors used in PSG which are collectively referred to as PSG sensors 223. The gas sensor 222 can be a CO2 gas sensor. The PSG sensors 223 can include one or more sensors that are used to obtain at least one physiological signal and/or at least one neurological signal. For example, the physiological signals include one or more of ECG, EOG, and EMG signals and the neurological signal includes one or more of EEG and Peripheral Neurophysiological Examination (PNE) signals. These signals can be measured using electrodes that are placed at certain locations on the user 210 as is known by those skilled in the art. The CO2 signal is also a physiological measurement that can be obtained. The PSG signals can also be pre-processed as is known by different channels of the amplifier 224 and the band-pass filter 226 to reduce noise for these particular signals before these signals are sent to the processor 228 for further analysis. The settings for the amplification and filtering of the PSG signals are known to those skilled in the art. In embodiments which only detect respiratory failure and take reactive actions the gas sensor 222 and the PSG sensor(s) 223 are not included in the system 200.

Figure 3:
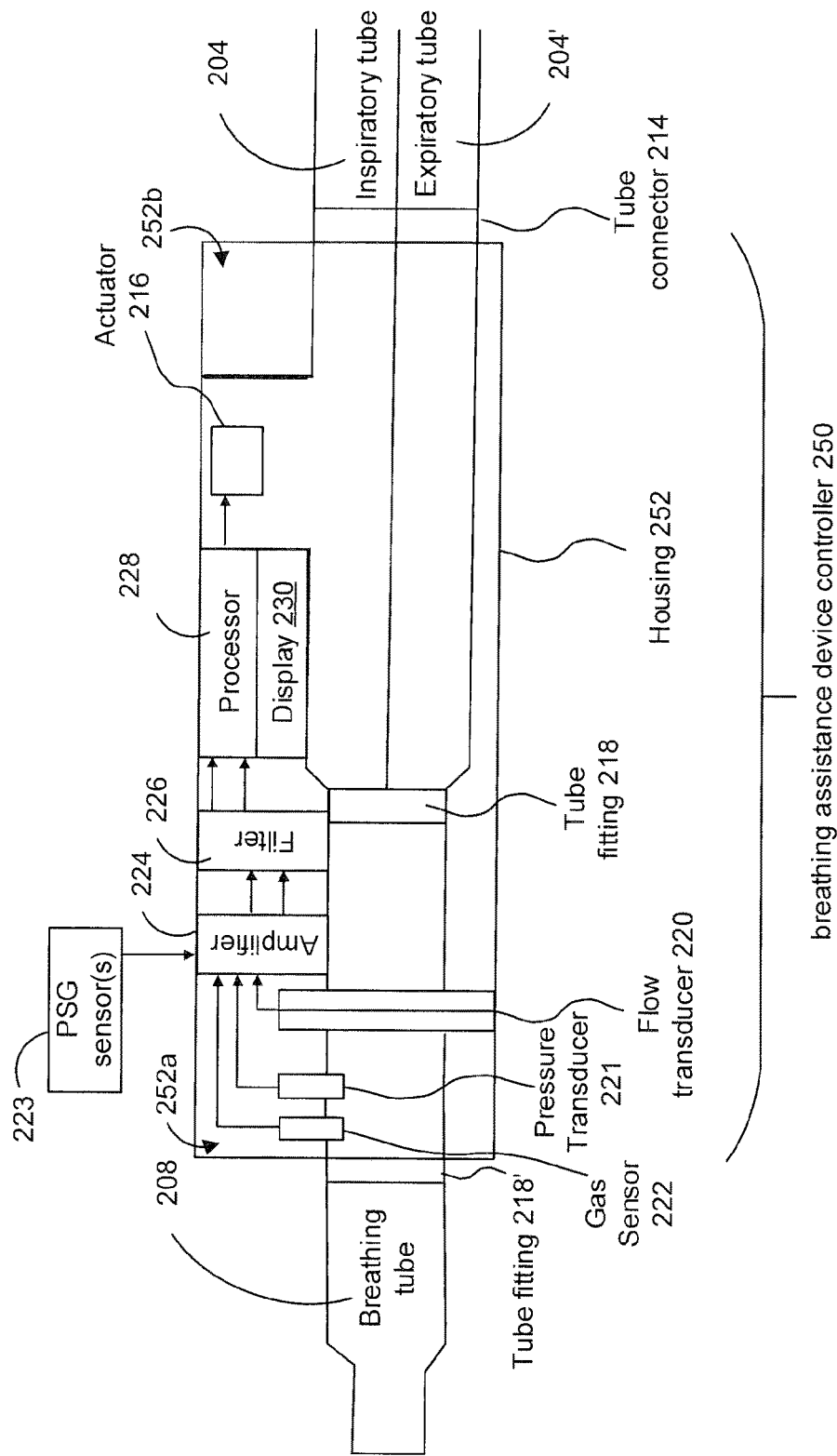
FIG. 3 is a block diagram of an example embodiment of a breathing assistance device controller that can be used with the breathing assistance system.

FIG. 3 shows an example embodiment of an integrated breathing assistance device controller 250 in which the various components needed for monitoring airflow and controlling the breathing assistance device 202 are fitted within a single device so as to allow the device to be used physically "inline" with the breathing assistance device 202. Hence the breathing assistance device controller 250 can be referred to as an inline device. The references numerals shown in FIG. 3 generally correspond to those described previously for the components shown in FIG. 2.

Furthermore, in embodiments in which the integrated breathing assistance device controller 250 is used in the prediction of when the user will experience respiratory failure, the controller 250 also includes the gas sensor 222 and it can be coupled to the PSG sensor(s) 223. In some embodiments the signals measured by the PSG sensor(s) 223 can be wirelessly transmitted to the sensor(s) integrated breathing assistance device controller 250 which will include a wireless communication radio or short range communication module such as a BlueTooth module (both not shown), for example. Accordingly, in embodiments which only detect respiratory failure and take reactive actions the gas sensor 222 and the PSG sensor(s) 223 are not included in the integrated breathing assistance device controller 250.

The breathing assistance device controller 250 has a housing 252 with first and second ends 252a and 252b. The end 252b can be fitted to the inspiratory tube 204 and the expiratory tube 204' via a tube connector 214. The end 252a may be attached to the breathing tube 208 using a tube fitting 218' to provide ventilation to the user 210. It should be noted that the junction (i.e. tube connector 214) that joins the inspiratory tube 204 and the expiratory tube 204' is internal to the device 250, and the tube fitting 218 is also internal to the device 250. Therefore, in some embodiments, the breathing assistance device controller 206 can be regarded as an enhanced tube adaptor to fit, connect or join breathing tube 208 to the inspiratory tube 204 and the expiratory tube 204'. However, it should be noted that there is no expiratory tube 204' when the breathing assistance device controller 250 is used with a CPAP machine as expiration is vented to the atmosphere in this case.

Figure 4:
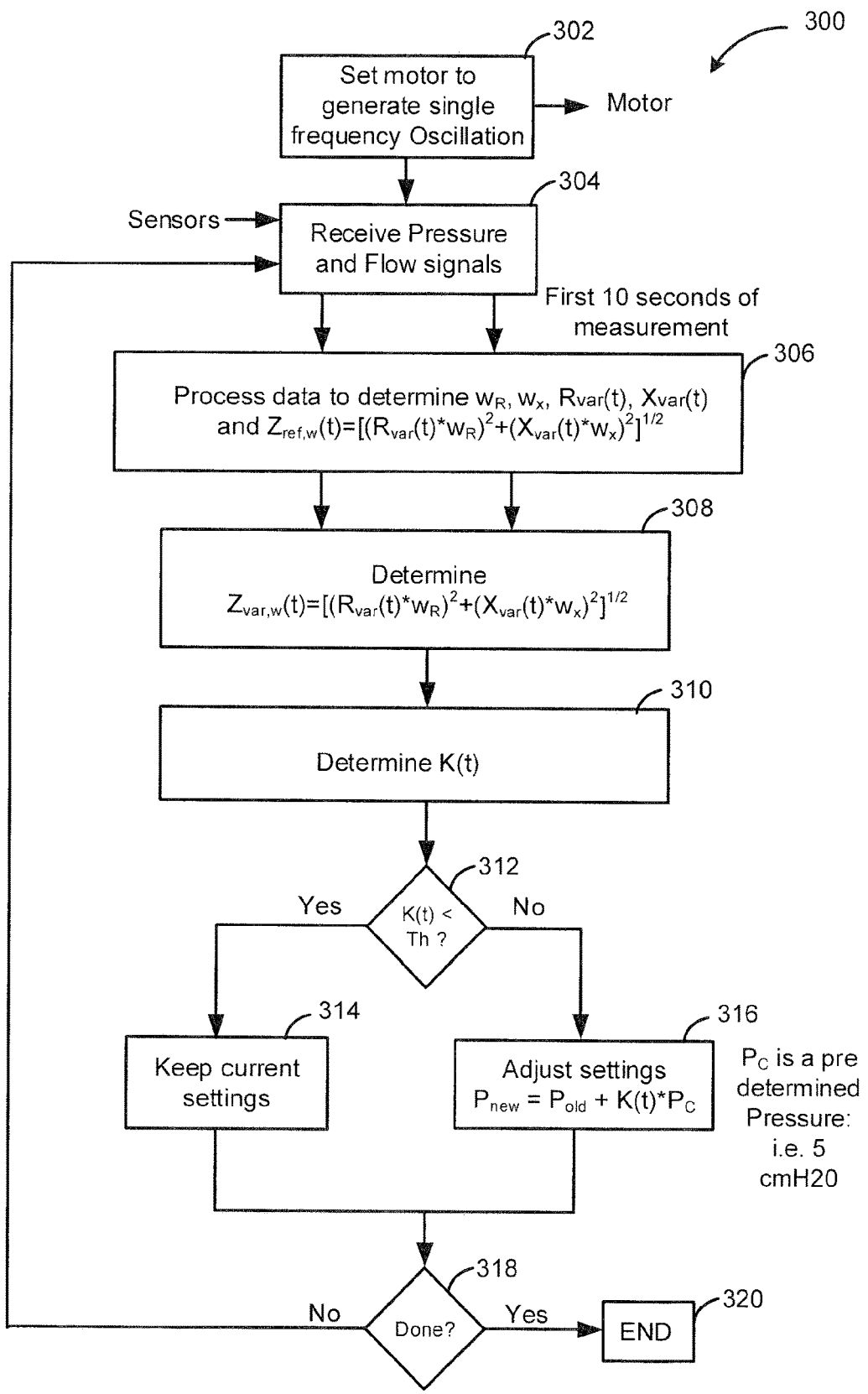
FIG. 4 is a flowchart of an example embodiment of a breathing assistance control method that utilizes respiratory failure detection to adjust the settings of a breathing assistance device in accordance with the teachings herein.

Referring now to FIG. 4, shown therein is a flowchart depicting an example embodiment of a breathing assistance control method 300 that can be used to acquire pressure and airflow measurements and use the measurements to detect when respiratory failure is occurring for a user and to control the operation of a breathing assistance device to stop or reduce the user's respiratory failure. For ease of explanation, the elements depicted in the breathing assistance system 200 shall be used in describing the various steps of the method 300. However, it should be understood that this technique can be used on the integrated breathing assistance device controller 250.

The method 300 may begin when the breathing assistance device 202 has been activated, and is supplying an airflow to the user 210. Starting at act 302, the processor 228 may operate the actuator 216 (e.g. motor) to generate an oscillation pressure signal having one or more oscillation frequencies within a desired frequency range. For example, in some embodiments the desired frequency range can be any frequency between 0.01 Hz-1 THz. As mentioned previously, the oscillation may be a single frequency oscillation. However, in other embodiments, the oscillation pressure signal may comprise a number of oscillation frequencies (i.e. where the oscillation is not sinusoidal). Act 302 can be done on a continuous or periodic basis as explained previously.

At act 304, sensors in the breathing assistance device controller 206 such as the flow transducer 220 and the pressure transducer 221 measure the flow rate and pressure, respectively, of the airflow (including the perturbation) that is sent to the user. The detected signals may be amplified by the amplifier 224 and filtered by, in this case, band-pass filter 226 with a center-frequency corresponding the frequency of the oscillation produced by the actuator 216. Also noted previously, in some embodiments, the passband may be made sufficiently narrow such that a notch filter can be used instead when a single frequency is used in the FOT measurement.

After the signals have been processed by applying amplification and filtering, the processed signals are received by the processor 228 for further processing. At act 306 the processor 228 may use the measured signals to determine the volume V(t) of the airflow and the mechanical impedance of the user's respiratory system over time. The volume V(t) may be determined as the integral of the flow rate signal that is measured plus a known bias or constant volume. To determine, the mechanical impedance, the processor 228 can apply a windowing function to the processed flow rate and pressure signals to help enforce periodicity (i.e. to reduce leakage in the frequency domain) and subsequently perform the Fourier transform (e.g. via the fast Fourier Transform FFT) of these signals in each window. In some embodiments, the signal can be windowed for short periods, such as ⅙ seconds for a 6 Hz single frequency sinusoidal oscillation produced by the actuator 216. Under the uncertainty principle, a shorter period may lead to a loss of frequency resolution with a gain of time resolution. Generally a useful windowing period can correspond to an inverse of the maximum oscillation frequency used in the oscillation pressure signal to provide a short window that does not result in a loss of too much frequency resolution. In other embodiments, the window may be longer, such as 4 seconds, for example. It can be understood that the signals can be assumed to be sufficiently stationary due to the band-pass filtering, and because of the short windowing duration. In some embodiments, a Hanning-type or Hamming-type window can be used to further help enforce periodicity by reducing the signal amplitude near the window edges to reduce leakage in the frequency domain. In other embodiments, the windows can be overlapping windows (e.g. with a maximum of 50% overlap between adjacent windows). In other embodiments, other types of windows may be appropriate for use. For example, in some cases it may be possible to use rectangular windows.

Still at act 306, after the windowing function has been applied, the Fourier transform of the pressure and flow rate in each time window may be used to obtain an estimate of the average mechanical impedance $Z_{rs}$ in that time window. More specifically the mechanical impedance can be expressed as a ratio between the Fourier transforms of the pressure and flow rate signals in each window:

$$Z_{rs}(\omega) = \frac{P(\omega)}{Q(\omega)} \quad (1)$$

where $P(\omega)$ is the FFT of the measured pressure signal and $Q(\omega)$ is the FFT of the measured flow rate signal at the angular frequency $\omega=2\pi f$ where f is the oscillation frequency of the actuator 216. Equation 1 can be applied to determine impedance by using pressure and flow rate measured at the airway opening of the user 210.

The mechanical impedance $Z_{rs}$ is a complex quantity with a real part corresponding to respiratory resistance ($R_{rs}$) which can be largely due to airflow resistance of intrathoracic and extrathoracic airways, lung tissue and chest wall and an imaginary part corresponding to reactance ($X_{rs}$) which can arise from elastic properties of the lung and chest wall, and the inertia of the oscillating air. The impedance can thus be described as a sum of the real and imaginary parts as shown in equation 2.

$$Z_{rs}(\omega) = R_{rs}(\omega) + jX_{rs}(\omega) \quad (2)$$

The parameters $R_{rs}(\omega)$ and $X_{rs}(\omega)$ may be characterized by fitting various respiratory models to the measured data to identify various respiratory system characteristics. For example, a commonly used model is the Single Compartment Model in which $R_{rs}(\omega)$ may be assumed to be constant with frequency $\omega$ so that $$X_{rs}(\omega) = \omega I_{rs} - \frac{E_{rs}}{\omega},$$

where $E_{rs}$ and $I_{rs}$ can be idealized lumped elements that represent the elastance and inertance of the respiratory system, respectively. Accordingly, examples of respiratory system characteristics include reactance/elastance and also inertance.

It may be also noted that the determination of the resistance and reactance in each time window yields continuous functions with respect to time, $R_{var}(t)$ and $X_{var}(t)$, for the chosen frequency of oscillation. In cases where multiple frequencies are used in the FOT oscillation signal, then the resistance and reactance may be calculated in the manner described above for each frequency separately. A separate time course behavior of the $R_{var}(t)$ and $X_{var}(t)$ may be developed for each frequency considered for analysis. Alternatively, the mean values of $X_{var}$ may be examined for different frequencies by plotting the mean values of $X_{var}$ against oscillation frequency. Similarly, the same may be done for $R_{var}$. It may be noted that there may be a single band-pass filter that may be configured to sequentially filter each frequency separately or there may be multiple band-pass filters each tuned at a unique frequency from the set of oscillation frequencies that are used contemporaneously to perform filtering (e.g. a comb filter). As noted previously the volume, V(t) may be determined as the integral of the flow rate signal.

Still at act 306, the impedance that is determined according to equation (1) is repeatedly performed for an initial period of time to obtain a baseline for the impedance $Z_{ref,w}(t)$ of the user's respiratory system that is indicative of their normal, healthy, functioning respiratory system. This may be done in different ways and one example of how to determine the baseline weighted impedance $Z_{ref,w}(t)$ is to obtain a weighted measure according to equation (2):

$$Z_{ref,w}(t) = [(R_{var}(t)*w_R)^2 + (X_{var}(t)*w_x)^2]^{1/2} \quad (2)$$

where, $Z_{ref,w}(t)$ is the baseline weighted impedance over a monitoring time period, such as 10 seconds for example, although other time periods can be used such as 5 seconds, 20 seconds, and 60 seconds. When longer time periods are used, averaging can be used to reduce noise. For example, if the time used to collect data to determine the baseline measurements is 60 seconds, then averaging can be done six times to get a baseline reading for monitoring time periods of 10 seconds. The baseline weighted impedance value is determined during an initial monitoring time period when the user first starts to use the breathing assistance device 202. The benefit of determining the baseline reading on a per user basis is the personalization aspect. For example, two patients with the same physical size (e.g. height and mass) and the same gender may still have two different breathing patterns and will therefore have different baseline weighted impedance values.

The parameters $w_R$ and $w_X$ are weights that are applied to the determined resistance and reactance, respectively, during the monitoring time interval. The weights $w_R$ and $w_X$ can be determined based on the particular user in case they have a respiratory condition, such as asthma for example. One way that the weights may be implemented is to have a table of weights for different diseases (i.e. respiratory conditions) and different levels of severity for each disease (i.e. for each respiratory condition). The weights can be determined from literature studies and then the particular weights for a given respiratory condition are used for a particular user when that particular user has the respiratory condition. Alternatively, the weights can be determined on a per-user basis by performing an initial assessment on the user.

This initial assessment for the weight parameters may be done to determine which of the resistance or the reactance is more important for the particular user and then the weights can be associated based on that determination. For example, from measurements of mean X and mean R, the user may be categorized as having a particular respiratory condition such as, but not limited to, asthma, COPD, CF or snoring (for example snoring can be detected as a respiratory failure since the snoring may be an alert of an impending airway closure). Based on the respiratory condition category, the relative weighting of R and X for the user is determined using a database or a lookup table based on data for populations that have the same respiratory condition. As an example, $R_{var}$ may be weighted higher than $X_{var}$ in users who are categorized as having asthma while $X_{var}$ may be weighted higher than $R_{var}$ in users who are categorized as having COPD. Accordingly, a larger or smaller weight can be applied to reactance relative to the weight that is applied to resistance depending on whether the user has a particular respiratory condition and a certain severity level for that particular respiratory condition.

In alternative embodiments, the baseline weighted impedance value can be redetermined at regular intervals after the initial baseline weighted impedance has been determined. For example, the baseline weighted impedance can be determined every 5 minutes, 10 minutes, 30 minutes, 60 minutes of more. The frequency of determining revised and up to date baseline weighted impedance values may be determined based on whether the user is suffering from some type of chronic respiratory condition. For example, if the patient is suffering from severe sleep apnea, the first 5 minutes of sleep may be a good reference for the rest of the night. However, if the patient is suffering from COPD or severe asthma, the weights may be determined before the patient falls asleep and more regularly, i.e. every 5 minutes. This is due to the nature of the disease and the fact that asthma and COPD are small airway disease, but sleep apnea is an upper airway disease.

It should be noted that in cases where the user suffers from a chronic respiratory condition then the baseline weighted impedance value may be determined for the user right after the user has undergone some treatment and their respiratory system is operating normally. The treatment may include inhaled medicine from an air puffer, taking other drugs or receiving treatment from other devices to help expand the airways, and possibly loosen and expel mucus from their lungs. Alternatively, the baseline weighted impedance value may be obtained from using standard breathing patterns that are expected for that user based on standard breathing patterns for a healthy population who have comparable physiological characteristics as the user, such as weight (within +/−10%), height (within +/−10%), and gender. Alternatively, the baseline weighted impedance value may be obtained by using the standard breathing patterns and also performing some measurements after the user has received treatment.

The method 300 then proceeds to act 308 where continuous monitoring of the weighted impedance $Z_{var,w}(t)$ is performed while the method 300 is being implemented by the breathing assistance device 202 until the method ends at act 320. In particular at act 308, the current weighted impedance $Z_{var,w}(t)$ for the current monitoring time period is determined according to equation (3):

$$Z_{var,w}(t)=[(R_{var}(t)*w_R)^2+(X_{var}(t)*w_x)^2]^{1/2} \quad (3)$$

It can be seen that equation (3) is similar to equation (2) in that the same weights are applied but this is done for the $R_{var}(t)$ and $X_{var}(t)$ for the current time period.

The method 300 then proceeds to act 310 where the value for a time varying respiratory index K(t) (i.e. a respiratory index signal) is determined based on a combination of the baseline weighted impedance $Z_{ref,w}(t)$ the current weighted impedance $Z_{var,w}(t)$. For example, the index K(t) can be determined based on a deviation of the current weighted impedance $Z_{var,w}(t)$ relative to the baseline weighted impedance $Z_{ref,w}(t)$, an example of which is shown in equation 4:

$$K(t) = SSE\ (Z_{var,w(t)}\ \text{and}\ Z_{ref,w(t)}) = \frac{\Sigma(Zvar, w(t) - Zref, w(t))^2}{\Sigma(Zref, w(t))^2} \quad (4)$$

so that the respiratory index signal K(t) is normalized to 1. It should be noted the above method for determining the value of the index K(t) is provided as an example and that in alternative embodiments the index K(t) may be determined using other methods. For example, the index K(t) may be determined using the normalized summed standard deviation of $Z_{var,w}(t)$ relative to $Z_{ref,w}(t)$. Alternatively, other statistical methods may be applied to determine/track changes in $Z_{var,w}(t)$ relative to $Z_{ref,w}(t)$. It should be noted that the index signal is in terms of an index n which is an integer corresponding to the number of the monitoring time period relative to the first monitoring time period that the method was applied to. Therefore, each time period contains a number of data points that are used to define a single index value for that particular time period.

The method 300 then proceeds to act 312 where the index K(t) is compared to a threshold value Th. The value of the threshold Th can be obtained from a table of thresholds that are defined for detecting each respiratory failure condition based on experimental or population data. Accordingly, the index value K(t) for the user's breathing pattern for the current monitoring time period is used to detect (or predict as in method 400) respiratory failure and the index value K(t) may be used to tailor the treatment (i.e. adjust the settings of the breathing assistance device according to the user's needs). If the index K(t) is smaller than the threshold value then this indicates that the user is not experiencing any respiratory failure or that there are no significant changes in the user's respiratory health. In this case the method 300 proceeds to act 314 where the current settings for the breathing assistance device 202 are maintained.

However, if the index K(t) is larger than the value of the threshold Th then the comparison of the index K(t) to the threshold value indicates that the user may be experiencing respiratory failure or there has been some other significant change in their respiratory health during the current monitoring time period. In this case, the method 300 proceeds to act 316 where the settings for the breathing assistance device are changed so that the user's respiratory health improves and they no longer experience the respiratory failure they were previously experiencing. The adjustments may be made in various ways. The actual way of adjusting the operation of the breathing assistance device 202 may depend on the user's baseline respiratory health. One example of adjusting the operation of the breathing assistance device 202 is to update the pressure according to some method such as multiplying a pre-determined pressure factor by the index value K(t) for the next monitoring time period and applying the result to the old pressure ($P_{old}$) to determine a new pressure ($P_{new}$). As an example, the pre-determined pressure factor may be 5 cmH$_2$O. The amount of the predetermined pressure factor can be determined based on whether the user currently has a chronic respiratory condition. For example, mild sleep apnea may be reduced by applying an air flow with a pressure of 5 cmH$_2$O using the breathing assistance device 202. However, sever sleep apnea may require an air flow with a pressure of 10 cmH$_2$O using the breathing assistance device 202. On the other hand, for a COPD patient a Non-Invasive Ventilation (NIV) device may be used with pre-determined bi-level pressures of 5 and 15 cmH2O, which is acceptable as the pressure range that is typically used for these devices ranges from about 0 to 20 cm H$_2$O. The pressure can be determined with measurements when the patient is not dealing with the chronic condition (i.e. measurements may be performed during the day when the patient is not sleeping) or based on a table from the literature that determines the level of pressure that is suitable for the patient given certain patient characteristics and/or severity of the chronic condition. Alternatively, a medical doctor, such as a family doctor, respirologist or sleep doctor, may decide the pressure level and prescribe it for the patient also based on the literature.

After the method 300 has performed act 314 or 316, the method 300 proceeds to act 318 where it is determined whether the method 300 should keep operating. If the condition at act 318 is true then the method 300 proceeds to act 320 and ends. If the condition at act 318 is not true then the method 300 goes to act 304 and continues to obtain sensor values, monitors the current weighted impedance, generates the index value and compares it to the threshold to determine when the user is experiencing any respiratory failure and if so, to update the operation of the breathing assistance device 202 to reduce or stop the respiratory failure.

Figure 5:
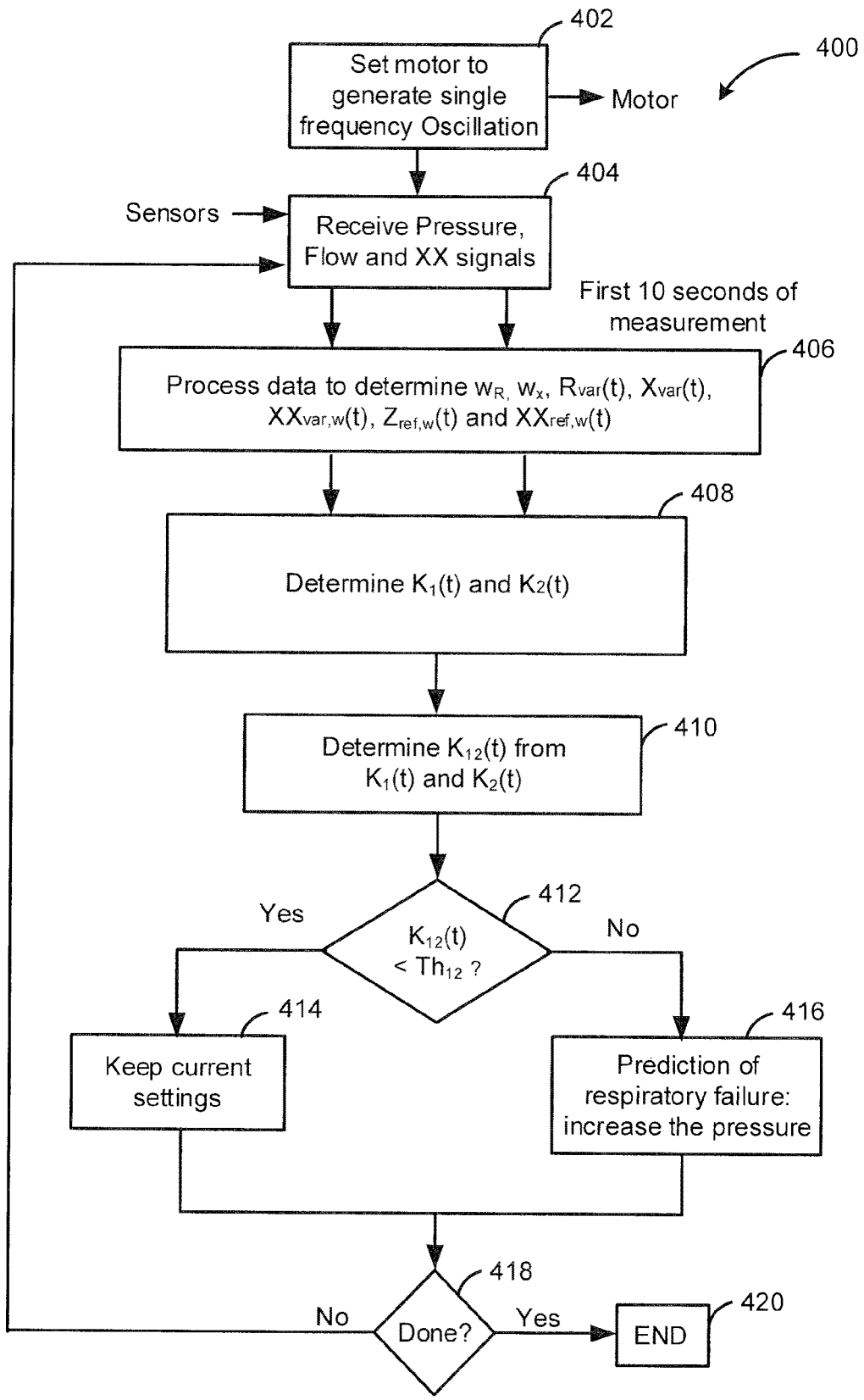
FIG. 5 is a flowchart of an example embodiment of a breathing assistance control method that utilizes respiratory failure prediction to adjust the settings of a breathing assistance device in accordance with the teachings herein.

Referring now to FIG. 5, shown therein is a flowchart depicting an example embodiment of a breathing assistance control method 400 that can be used to acquire pressure and airflow measurements and at least one other physiological measurement and use the measurements to predict when respiratory failure is occurring for a user and to take pro-active action to control the operation of a breathing assistance device to prevent the predicted respiratory failure from occurring. As in the description of FIG. 4, for ease of explanation, the elements depicted in the breathing assistance system 200 shall be used in describing the various steps of the method 400. However, it should be understood that this technique can be used on the integrated breathing assistance device controller 250.

The method 400 begins in a similar fashion as the method 300 when the breathing assistance device 202 has been activated, and is supplying an airflow to the user 210. Act 402 is the same as act 302 for performing FOT and act 404 is similar to act 304, in that sensors, such as the flow transducer 220 and the pressure transducer 221, are used to measure the flow rate and pressure, respectively, of the airflow (including the perturbation) that is sent to the user and these measured signals are preprocessed in a similar manner as those obtained at act 304. However, act 404 is different than act 304 in that act 404 also includes obtaining at least one PSG signal which is denoted by XX. The PSG signals XX include one or more of CO2, O2 and/or some other gas in the user's expired breath, the user's ECG (i.e. brain activity), EOG (i.e. eye movements), and EMG (i.e. skeletomuscular activity). These signals can be measured as described previously. The PSG signals are now used in addition to the measurements of pressure and flow of breathing to predict respiratory failure. This is in contrast to the method 300 of FIG. 4 where only the measurement of pressure and flow of breathing were used to detect respiratory failure.

After the signals have been processed by applying amplification and filtering, the processed signals are received by the processor 228 for further processing. At act 406 the processor 228 may determine the volume V(t) of the airflow and the mechanical impedance of the user's respiratory system over time as was described for act 306 of method 300 in terms of using windows and frequency transforms for analyzing the data to obtain an estimate of the average mechanical impedance $Z_{rs}$ as well as the resistance $R_{rs}(t)$ and reactance $X_{rs}(t)$ for the various time windows of data that are analyzed. Act 406 also determines the weight parameters $w_R$ and $w_X$ for resistance and reactance, respectively, the baseline weighted impedance $Z_{ref,w}(t)$ and the current weighted impedance $Z_{var,w}(t)$ in the various time windows of data that are analyzed in a similar manner as was described for act 306. However, act 406 is different than act 306 in that act 406 also includes determining a baseline weighted PSG signal $XX_{ref,w}(t)$ and the current weighted PSG signal $XX_{var,w}(t)$ for the additional physiological and/or neurological signals XX. When the baseline weighted PSG signal $XX_{ref,w}(t)$ and the current weighted PSG signal $XX_{var,w}(t)$ are determined using at least two PSG signals, these PSG signals are combined in some fashion. For example, since there are multiple streams of time series data, the cross-correlation, the Cross-Spectral density or the Coherence of pairs of data streams can be determined providing a richer mode of analysis as this will indicate relationships between pairs frequencies or pairs of data streams. For example, the coherence between pressure and flow data may yield a value between 0 and 1 which may be used as a time series data that can be used for further analysis.

The method 400 then proceeds to act 408 where continuous monitoring of the current weighted impedance $Z_{var,w}(t)$ and the current weighted PSG signal $XX_{var,w}(t)$ is performed while the method 400 is being implemented by the breathing assistance device 202 until the method ends at act 420. The current weighted impedance $Z_{var,w}(t)$ may be obtained according to equation (3). The current weighted PSG signal $XX_{var,w}(t)$ is obtained using the same equation as for $XX_{ref,w}(t)$ except that the calculations are done using data from the current time window.

Act 408 also includes determining values for a first time varying index $K_1(t)$ (i.e. a first index signal) that is based on respiratory status and a second time varying index $K_2(t)$ (i.e. a second index signal) that is based on PSG status. For example, the first index $K_1(t)$ may track the deviation of the current weighted impedance relative to the baseline weighted impedance according to equation (5). The second index $K_2(t)$ may track the deviation of the current weighted PSG signal relative to the baseline weighted PSG signal according to equation (6).

$$K_1(t) = \frac{\Sigma(Zvar, w(t) - Zref, w(t))^2}{\Sigma(Zref, w(t))^2} \qquad (5)$$

$$K_2(t) = \frac{\Sigma(XXvar, w(t) - XXref, w(t))^2}{\Sigma(XXref, w(t))^2} \qquad (6)$$

Equations (5) and (6) are provided as examples and there may be other techniques of determining the indices $K_1(t)$ and $K_2(t)$. Based on equations (5) and (6) $K_1(t)$ and $K_2(t)$ are normalized to have a magnitude that is less than or equal to 1. In other embodiments other equations can be used instead of equations (5) and (6) for determining the index signals $K_1(t)$ and $K_2(t)$.

The method 400 then proceeds to act 410 where the first and second index signals $K_1(t)$ and $K_2(t)$ are combined to create the respiratory index signal $K_{1,2}(t)$. This combination can be done according to equation (7a) or equation (7b).

$$K_{1,2}(t) = K_1(t) * K_2(t) \qquad (7a)$$

$$K_{1,2}(t) = K_1(t)/(K_1(t)+K_2(t)) + K_2(t)/(K_1(t)+K_2(t)) \qquad (7b)$$

Alternatively, the combination of $K_1(t)$ and $K_2(t)$ into $K_{1,2}(t)$ can be done using another technique. The respiratory index $K_{1,2}(t)$ is different from the respiratory index K(t) in that the respiratory index $K_{1,2}(t)$ is used in the prediction of respiratory failure while the respiratory index K(t) is used in the detection of respiratory failure.

The method 400 then proceeds to act 412 where the index $K_{1,2}(t)$ is compared to a threshold value $Th_{1,2}$. The threshold value $Th_{12}$ can be obtained from a table of thresholds that are defined for predicting each respiratory failure condition based on experimental or population data. If the respiratory index $K_{1,2}(t)$ is smaller than the threshold value then this indicates that the user is not likely to be developing respiratory failure in the imminent future (e.g. in the next tens of seconds to a minute or so). In this case the method 400 proceeds to act 414 where the current settings for the breathing assistance device 202 are maintained.

However, if the index $K_{1,2}(t)$ is larger than the threshold value then this indicates that the comparison of the respiratory index to the threshold value has predicted that the user is likely to be developing respiratory failure in the imminent future (e.g. in the next tens of seconds to a minute or so). In this case, the method 400 proceeds to act 416 where the settings for the breathing assistance device 202 are changed to reduce the likelihood that the user will experience the predicted respiratory failure. The adjustments may be made in various ways. The actual way of adjusting the operation of the breathing assistance device 202 may depend on the user's baseline respiratory health. For example, in the case where the predicted respiratory failure is sleep apnea the breathing assistance device 202 can be controlled so that the user avoids zero flow in their respiratory system. For instance, in the case of severe sleep apnea, the increase in pressure may have to be more aggressive (i.e. steps of 5 $cmH_2O$) in order to prevent the apnea from occurring. However, for mild sleep apnea, an increase in 1 cm $H_2O$ of pressure may prevent the apnea event from occurring.

After the method 400 has performed act 414 or 416, the method 400 proceeds to act 418 where it is determined whether the method 400 should keep operating. If the condition at act 418 is true then the method 400 proceeds to act 420 and ends. If the condition at act 418 is not true then the method 400 goes to act 404 and continues to obtain sensor values, monitor the current weighted impedance and current weighted PSG, generate the two index values $K_1(t)$ and $K_2(t)$ and combine them into the respiratory index signal $K_{1,2}(t)$, compare $K_{1,2}(t)$ to the threshold to predict when the user is likely to soon experience respiratory failure and update the operation of the breathing assistance device 202 to avoid the predicted respiratory failure.

The weight parameters ($w_r$ and $w_x$) can reflect the specific portion of the reactive/elastic part of the user's respiratory system that is distancing or deviating itself from the elastic part and influencing the resistive part instead (e.g. sometimes because other factors are involved such as the fact that resistance and elastance themselves are sinusoidally changing with breathing, the multiplication of sinusoidal elastance and sinusoidal volume may change the phase of a portion of the elastance to become in phase with air flow, and hence be more resistive). The result of this deviation can cause distress for the user since it may manifest physically as either an obstruction of their airways or a deep distress to their respiratory system due to various factors including, but not limited to, derecruitment of certain lung regions, increased heterogeneity of the user's lungs or the presence of liquid in the user's lungs. As such the determined parameters can thus be used to perform at least one of: tuning of the breathing assistance device 202 to minimize respiratory failure; diagnosis or identification of the presence of respiratory disease; and operating the breathing assistance device 202 to obtain therapeutic outcomes, for example, with respect to adjusting the operating parameters of the breathing assistance device 202 such as at least one of the pressure, flow rate, and moisture of the generated airflow to help COPD patients to breathe or expectorate.

Figure 8:
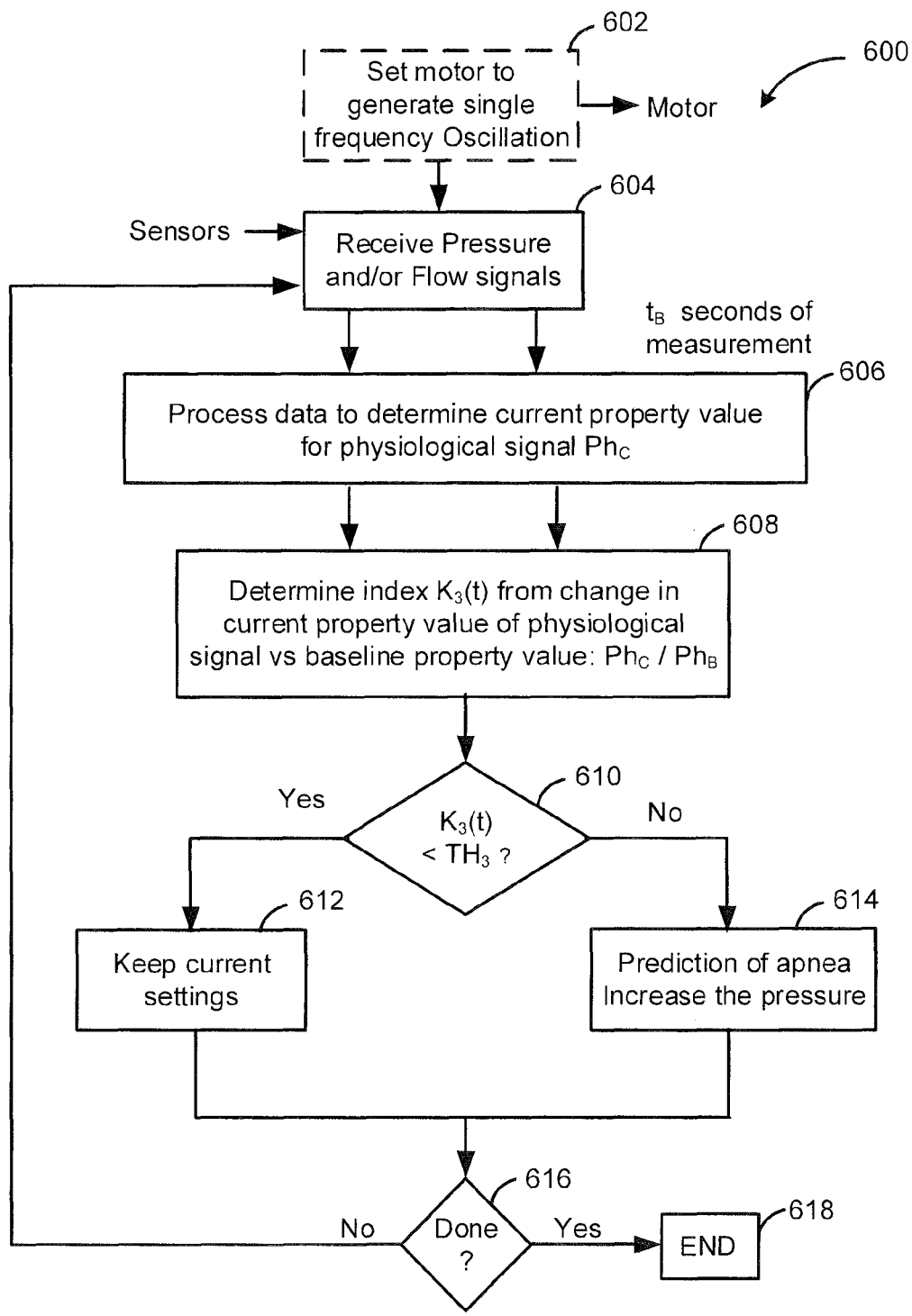
FIG. 8 is a flowchart of another example embodiment of a breathing assistance control method that utilizes respiratory failure prediction to adjust the settings of a breathing assistance device in accordance with the teachings herein.

Referring now to FIG. 8, shown therein is a flowchart depicting another example embodiment of a breathing assistance control method 600 that can be used to acquire pressure and airflow measurements, to use the measurements to predict when respiratory failure is occurring for a user and to take proactive action to control the operation of a breathing assistance device to prevent the predicted respiratory failure from occurring. As in the description of FIGS. 4 and 5, for ease of explanation, the elements depicted in the breathing assistance system 200 shall be used in describing the various steps of the method 600. However, it should be understood that this technique can be used on the integrated breathing assistance device controller 250.

The method 600 begins in a similar fashion as methods 300 and 400 when the breathing assistance device 202 has been activated, and is supplying an airflow to the user 210. Act 602 is the same as acts 302 and 402 for performing FOT but it should be noted that act 602 may be optional when the physiological parameters being used to predict a respiratory failure do not need the FOT technique in order to be measured. For example, the physiological measurements that may be used with method 600 can be one of flow rate, pressure and tidal volume in which case the FOT method is not required and act 602 can be skipped. Alternatively, the physiological measurements that may be used with the method 600 may also be one of resistance, reactance and impedance in which case act the FOT method of act 602 is performed.

Act 604 may be slightly different compared to act 304 in that it may include receiving just one of the pressure and flow signals rather than both of them depending on the physiological parameter which is being used to perform the respiratory failure prediction. For example, if pressure is being used to predict respiratory failure then only the pressure signal is measured and received. Alternatively, if physiological parameters like resistance, reactance or impedance is being used to predict respiratory failure then both the flow rate and the pressure signals are measured and received at act 604. In each of these case, the signals can be measured as described previously.

After the signals have been processed by applying amplification and filtering as required, as described earlier, the processed signals are received by the processor 228 for further processing. At act 606, the processor 228 determines a baseline value for the physiological parameter for a certain period of time before the occurrence of a respiratory failure. This may be determined by performing sleep studies on the user, collecting a plurality of time segment data for determining the physiological parameter in which each time segment includes a baseline time period before the occurrence of a respiratory event, determining a baseline property value for a property of the physiological parameter and then during actual use determining a current property value for the property and comparing the current property value to the baseline property value to determine if there is a large enough change to predict that a respiratory failure is likely to be imminent.

The inventors have determined that the determination made at act 606 may be used to predict an imminent respiratory failure based on sleep study data obtained from patients including a first study using data from CPAP memory cards for 10 patients who suffer from severe sleep apnea including 8 males and 2 females with an overall average age of 53 years and a second study using data from 7 hospital patients who were all male, suffer from severe sleep apnea and have an overall average age of 51 years. For the second study group, all of the data were recorded for a single night so the number of sleep apnea events for the patients in the second study group were lower than the number of sleep apnea events in the data obtained from the CPAP memory cards; however, the data from the second study group contained FOT data for FOT tests that were continuously done during the one night test. While all of the data had sleep apnea events, it is believed that the findings are applicable to other types of respiratory failures. This is because it was generally found that there was a significant difference in spectral density characteristics in signals recorded previous to a respiratory failure occurring compared to signals recorded when breathing was healthy for different types of respiratory conditions. For example, this was found in airflow data and impedance data for patients that had sleep apnea as well as other patients that had other respiratory conditions such as expiratory flow limitation associated with COPD that was showing up both in airflow data and the impedance data.

Figure 9:
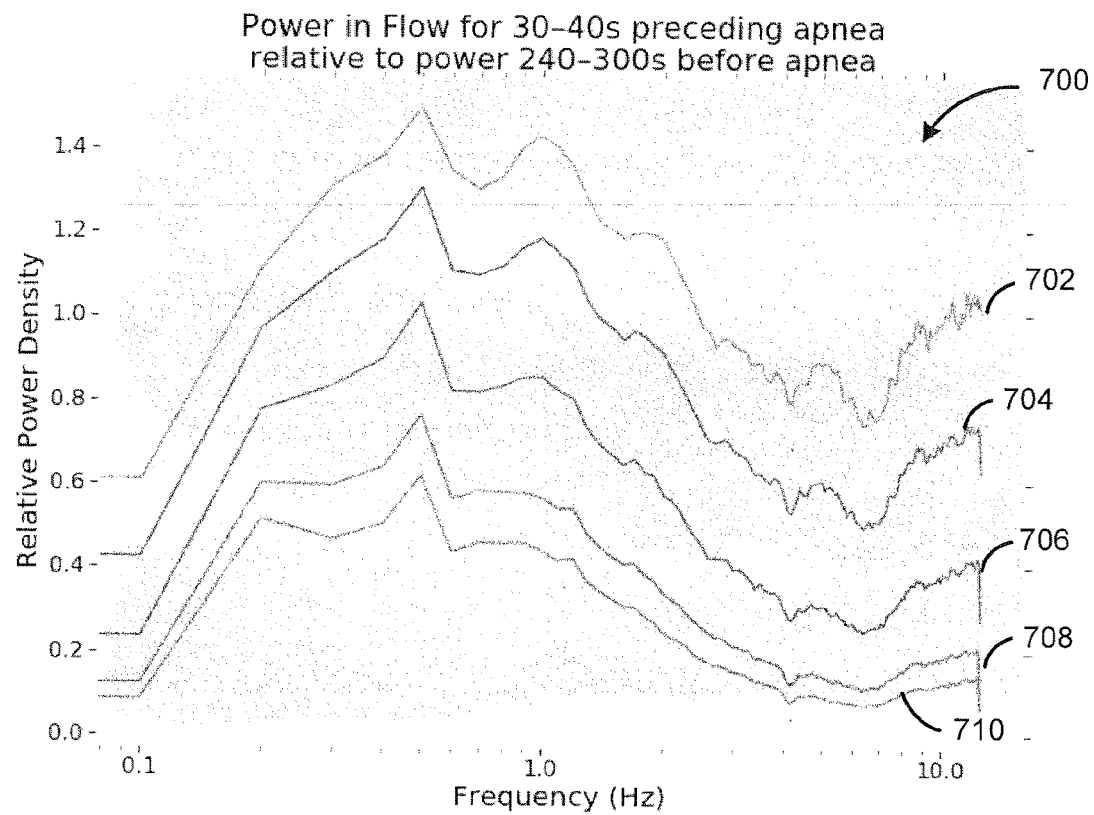
FIG. 9 is a chart showing curves at various percentiles for changes in power for flow rate data obtained for a time period preceding an apnea event relative to a baseline time period obtained from a first patient that was representative of the general results observed from a group of patients.

For example, referring now to FIG. 9, shown therein is chart showing curves 700 at various percentiles for changes in power for flow rate data obtained for a time period of 10 seconds (from about 30 to 40 seconds) preceding an apnea event relative to a baseline time period of about 60 seconds (from about 240 to 300 seconds) before the apnea event obtained from a first patient from the first study group that was representative of the general results observed from all of the patients. The data was obtained from this first patient over a two year time span in which there were 9,494 obstructive sleep apnea events. The curves were obtained by determining the power spectral density for the current flow rate data and dividing by the power spectral density for the baseline flow rate data. The curves 702, 704, 706, 708 and 710 represent the $75^{th}$ percentile (upper quartile), $68^{th}$ percentile, median, $32^{nd}$ percentile and the $25^{th}$ percentile, respectively and the x-axis is shown with a logarithmic scale. From the curves 702 to 710 it can be seen that at 0.4 Hz, there is a peak in relative power spectral density. Therefore, for this particular patient, the relative power spectral density at 0.4 Hz of the current flow rate data versus the baseline flow rate data can be compared to a threshold and when the relative power spectral density is above the threshold it is indicative that a sleep apnea event is likely to be imminent. This was also seen in other patients in the study and may be used for this patient population but in alternative embodiments different frequencies at which to determine the power spectral density may be used as well as different thresholds for different patient populations (e.g., based on at least one of age, sex, type of respiratory condition and severity of respiratory condition). In another alternative embodiment, the frequency at which the power spectral density measurement is made as well as the threshold value may be personalized on a patient by patient basis for improved performance. Accordingly, in at least one embodiment the physiological respiratory signal is flow rate for the air provided to the patient and the property is power spectral density and a respiratory index value can be determined from the relative power spectral density. It can be seen that the relative power spectral density changes consistently and is significantly reduced in the frequency range <0.2 Hz and the frequency range >2 Hz, at about 40 seconds before the sleep apnea event.

It should be noted that these results were also observable for other time periods before an actual respiratory failure event so that the time period of 10 seconds (from about 30 to 40 seconds) can be expanded to about 100 seconds before a respiratory failure and instead of doing the analysis for 10 seconds it might be for time period of about 0.1 to 120 seconds, or about 0.1 to 60 seconds or about 5 to 60 seconds. This was also observed for the results obtained with the other physiological respiratory signals described in FIGS. 10 to 14.

Figure 10:
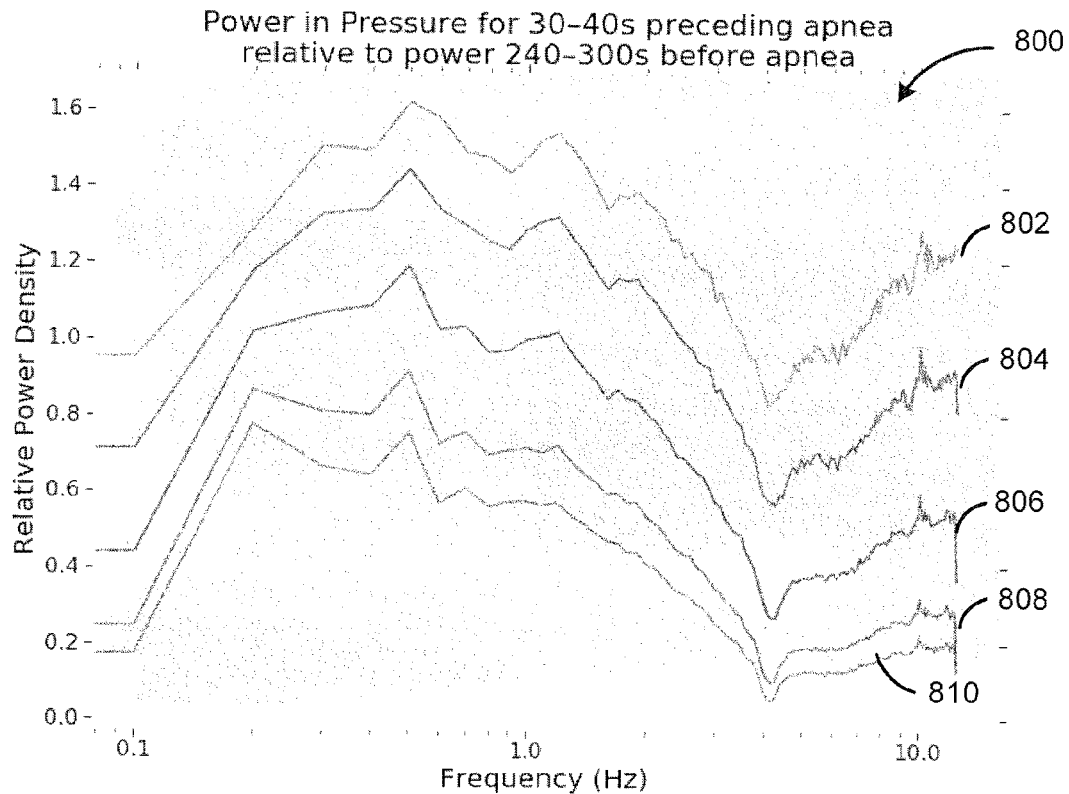
FIG. 10 is a chart showing curves at various percentiles for changes in power for pressure data for a time period preceding an apnea event relative to a baseline time period obtained from the first patient that was representative of the general results observed from a group of patients.

As another example, referring now to FIG. 10, shown therein is chart showing curves 800 at various percentiles for changes in power for pressure data obtained for a time period of 10 seconds (from about 30 to 40 seconds) preceding an apnea event relative to a baseline time period of about 60 seconds (from about 240 to 300 seconds) before the apnea event obtained from the first patient from the first study group. The curves are obtained by determining the power spectral density for the current pressure data and dividing by the power spectral density for the baseline pressure data. The curves 802, 804, 806, 808 and 810 represent the $75^{th}$ percentile (upper quartile), $68^{th}$ percentile, median, $32^{nd}$ percentile and the $25^{th}$ percentile, respectively and the x-axis is shown with a logarithmic scale. From the curves 802 to 810 it can be seen that at 0.5 Hz, there is a peak in relative power spectral density. Therefore, for this particular patient, the relative power spectral density at about 0.5 Hz of the current pressure data versus the baseline pressure data can be compared to a threshold and when the relative power spectral density is above the threshold it is indicative that a sleep apnea event is likely to be imminent. This was also seen in other patients in the study and may be used for this patient population but in alternative embodiments different frequencies at which to determine the power spectral density may be used as well as different thresholds for different patient populations (e.g., based on at least one of age, sex, type of respiratory condition and severity of respiratory condition). In another alternative embodiment, the frequency at which the power spectral density measurement is made as well as the threshold value may be personalized on a patient by patient basis for improved performance. Accordingly, in at least one embodiment, the physiological respiratory signal is pressure of the air flow provided to the patient and the property is power spectral density of the pressure. A respiratory index value can be determined from the relative power spectral density of the pressure. It can be seen that the relative power spectral density changes consistently and is significantly reduced in the frequency range <0.2 Hz and the frequency range >2 Hz, at about 40 seconds before the sleep apnea event.

Figure 11:
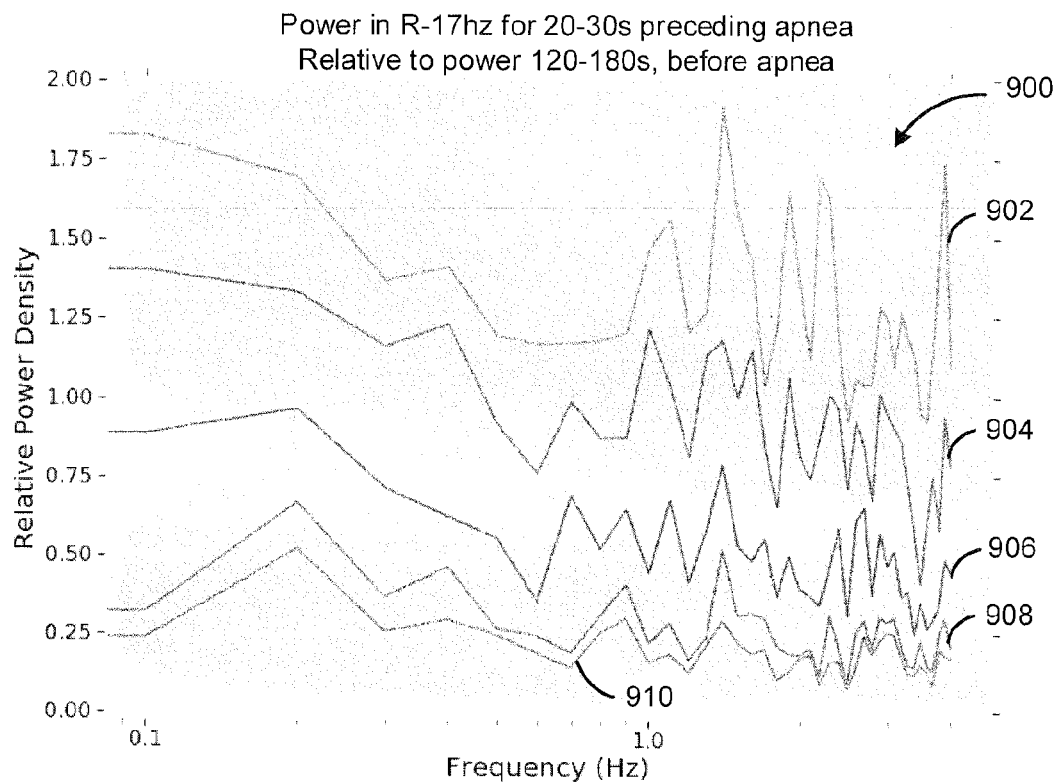
FIG. 11 is a chart showing curves at various percentiles for changes in power for resistance data of a physiological respiratory system for a time period preceding an apnea event relative to a baseline time period obtained from a second patient that was representative of the general results observed from a group of patients.

As another example, referring now to FIG. 11, shown therein is chart showing curves 900 at various percentiles for changes in power for resistance data obtained using a frequency of 8 Hz for the FOT method for a time period of 10 seconds (from about 30 to 40 seconds) preceding an apnea event relative to a baseline time period of about 60 seconds (from about 120 to 180 seconds) before the apnea event obtained from a second patient from a second study group. The curves are obtained by determining the power spectral density for the current resistance of the patient's respiratory system and dividing by the power spectral density for the baseline resistance data. The curves 902, 904, 906, 908 and 910 represent the $75^{th}$ percentile (upper quartile), $68^{th}$ percentile, median, $32^{nd}$ percentile and the $25^{th}$ percentile, respectively and the x-axis is shown with a logarithmic scale. From the curves 902 to 910 it can be seen that relative power spectral density is reduced below one for frequencies >0.4 Hz, up to about 30 seconds before apnea event. Therefore, for this particular patient, the relative power spectral density at about 0.4 Hz and higher (e.g. 0.5 Hz) of the resistance data versus the baseline resistance data can be compared to a threshold and when the relative power spectral density is below the threshold it is indicative that a sleep apnea event is likely to be imminent. This was also seen in other patients in the study and may be used for this patient population but in alternative embodiments different frequencies at which to determine the power spectral density may be used as well as different thresholds for different patient populations (e.g., based on at least one of age, sex, type of respiratory condition and severity of respiratory condition). In another alternative embodiment, the frequency at which the power spectral density measurement is made as well as the threshold value may be personalized on a patient by patient basis for improved performance. Accordingly, in at least one embodiment, the physiological respiratory signal is resistance (of the patient's respiratory system) and the property is power spectral density of the resistance. A respiratory index value can be determined from the relative power spectral density of the resistance. It can be seen that the relative power spectral density changes consistently and is significantly reduced below a threshold value in the frequency range >0.4 Hz (e.g. at about 0.5 Hz) at about 30 seconds before the sleep apnea event.

Figure 12:
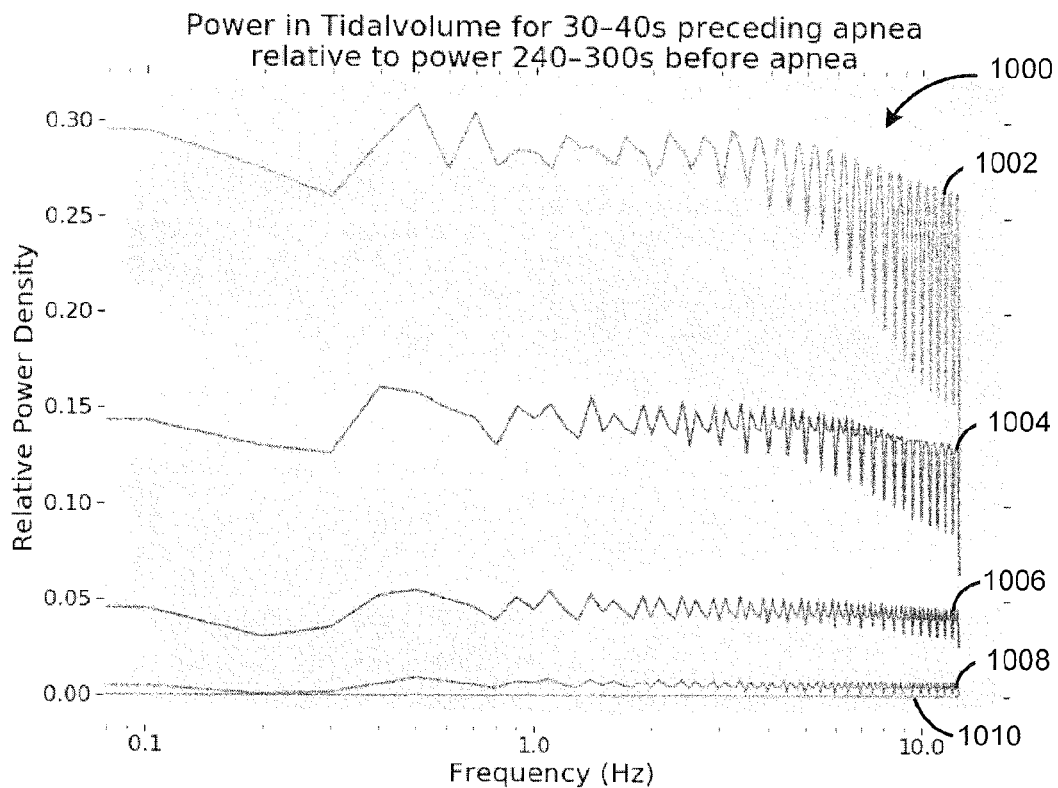
FIG. 12 is a chart showing curves at various percentiles for changes in power for tidal volume data for a time period preceding an apnea event relative to a baseline time period obtained from the first patient that was representative of the general results observed from a group of patients.

As another example, referring now to FIG. 12, shown therein is chart showing curves 1000 at various percentiles for changes in power for tidal volume obtained for a time period of 10 seconds (from about 30 to 40 seconds) preceding an apnea event relative to a baseline time period of about 60 seconds (from about 240 to 300 seconds) before the apnea event obtained from the first patient from the first study group. The curves are obtained by determining the power spectral density for the current tidal volume and dividing by the power spectral density for the baseline tidal volume data. The curves 1002, 1004, 1006, 1008 and 1010 represent the $75^{th}$ percentile (upper quartile), $68^{th}$ percentile, median, $32^{nd}$ percentile and the $25^{th}$ percentile, respectively and the x-axis is shown with a logarithmic scale. From the curves 1002 to 1010 it can be seen that the power of the tidal volume data is reduced across all frequencies, corresponding to a decrease in total tidal volume, about 30 s 40 s before apnea event. Therefore, for this particular patient, the relative power spectral density for a frequency range from 0 Hz to up to about 10 Hz of the current tidal volume data versus the baseline tidal volume data can be compared to a threshold of about 0.3 and when the relative power spectral density is below the threshold it is indicative that a sleep apnea event is likely to be imminent. This was also seen in other patients in the study and may be used for this patient population but in alternative embodiments different frequencies at which to determine the power spectral density may be used as well as different thresholds for different patient populations (e.g., based on at least one of age, sex, type of respiratory condition and severity of respiratory condition). In another alternative embodiment, the frequency at which the power spectral density measurement is made as well as the threshold value may be personalized on a patient by patient basis for improved performance. Accordingly, in at least one embodiment, the physiological respiratory signal is tidal volume of the air inspired by the patient and the property is power spectral density of the tidal volume. A respiratory index value can be determined from the relative power spectral density of the tidal volume. It can be seen that the relative power spectral density changes consistently and is significantly reduced below a threshold value in the frequency range from about 0 Hz to about 0.9 Hz at about 30 seconds before the sleep apnea event.

Figure 13:
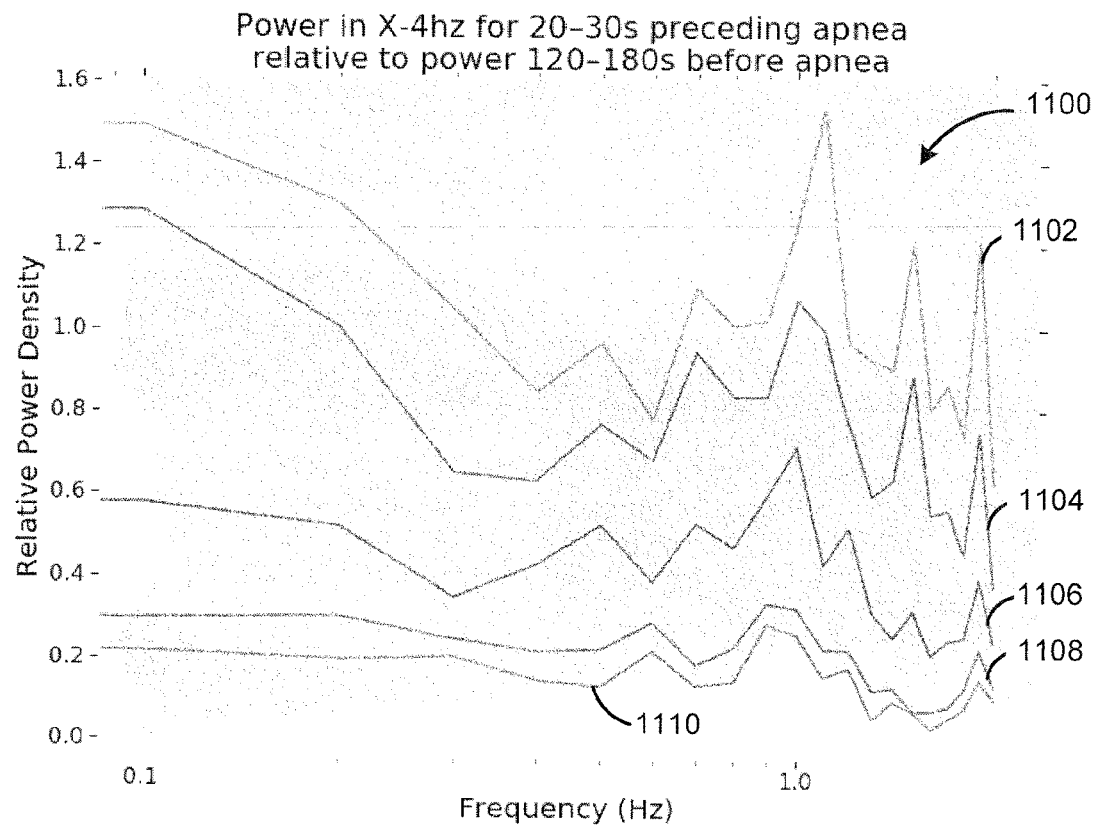
FIG. 13 is a chart showing curves at various percentiles for changes in power for reactance data of a physiological respiratory system for a time period preceding an apnea event relative to a baseline time period obtained from the second patient that was representative of the general results observed from a group of patients.

As another example, referring now to FIG. 13, shown therein is chart showing curves 1100 at various percentiles for changes in power for reactance data obtained using a frequency of 4 Hz for the FOT method for a time period of 10 seconds (from about 30 to 40 seconds) preceding an apnea event relative to a baseline time period of about 60 seconds (from about 120 to 180 seconds) before the apnea event obtained from the second patient from the second study group. The curves are obtained by determining the power spectral density for the current reactance of the patient's respiratory system and dividing by the power spectral density for the baseline reactance data. The curves 1102, 1104, 1106, 1108 and 1110 represent the $75^{th}$ percentile (upper quartile), $68^{th}$ percentile, median, $32^{nd}$ percentile and the $25^{th}$ percentile, respectively and the x-axis is shown with a logarithmic scale. From the curves 1102 to 1110 it can be seen that relative power spectral density is reduced across all frequencies, but most notably the 0.3-0.6 Hz range and >1.2 Hz, up to about 30 seconds before apnea event. Therefore, for this particular patient, the relative power spectral density from about 0.3 Hz to 0.6 Hz of the current reactance data versus the baseline pressure data can be compared to a threshold and when the relative power spectral density is below the threshold it is indicative that a sleep apnea event is likely to be imminent. This was also seen in other patients in the study and may be used for this patient population but in alternative embodiments different frequencies at which to determine the power spectral density may be used as well as different thresholds for different patient populations (e.g., based on at least one of age, sex, type of respiratory condition and severity of respiratory condition). In another alternative embodiment, the frequency at which the power spectral density measurement is made as well as the threshold value may be personalized on a patient by patient basis for improved performance. Accordingly, in at least one embodiment, the physiological respiratory signal is reactance (of the patient's respiratory system) and the property is power spectral density of the reactance. A respiratory index value can be determined from the relative power spectral density of the reactance. It can be seen that the relative power spectral density from about 0.3 to 0.6 Hz of the current reactance data versus the baseline pressure data is below a threshold at about 40 seconds before the sleep apnea event.

Figure 14:
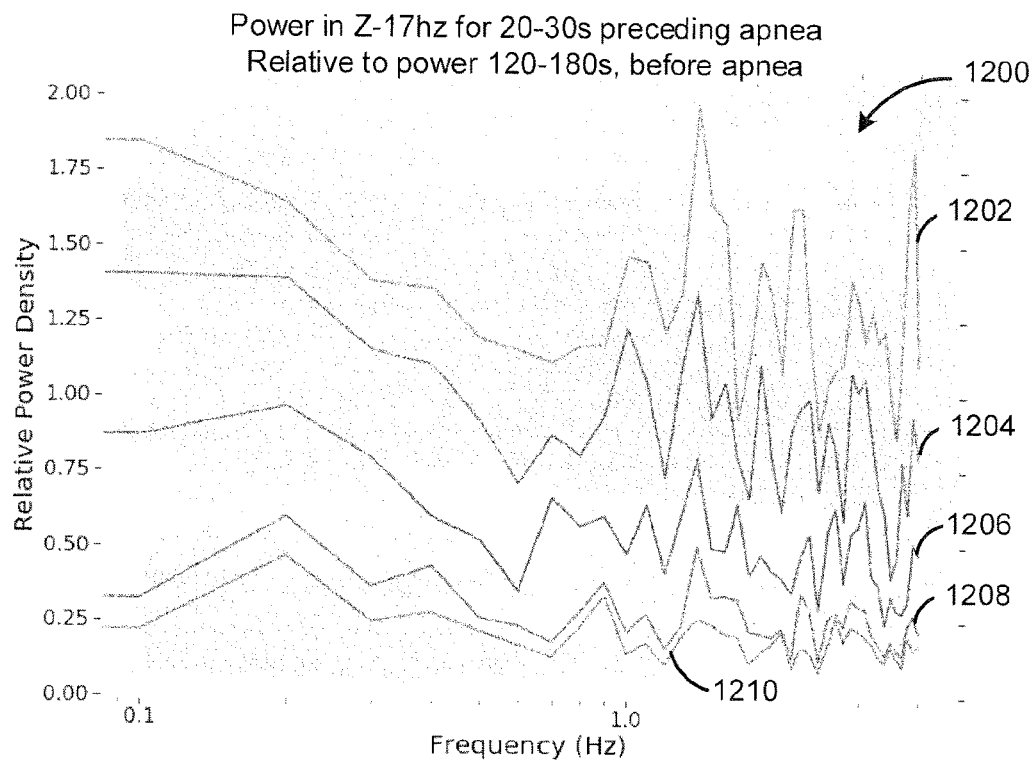
FIG. 14 is a chart showing curves at various percentiles for changes in power for impedance data of a physiological respiratory system for a time period preceding an apnea event relative to a baseline time period obtained from the second patient that was representative of the general results observed from a group of patients.

As another example, referring now to FIG. 14, shown therein is chart showing curves 1200 at various percentiles for changes in power for impedance data obtained using a frequency of 8 Hz for the FOT method for a time period of 10 seconds (from about 30 to 40 seconds) preceding an apnea event relative to a baseline time period of about 60 seconds (from about 120 to 180 seconds) before the apnea event obtained from the second patient from the second study group. The curves are obtained by determining the power spectral density for the current reactance of the patient's respiratory system and dividing by the power spectral density for the baseline reactance data. The curves 1202, 1204, 1206, 1208 and 1210 represent the $75^{th}$ percentile (upper quartile), $68^{th}$ percentile, median, $32^{nd}$ percentile and the $25^{th}$ percentile, respectively and the x-axis is shown with a logarithmic scale. From the curves 1202 to 1210 it can be seen that relative power spectral density is reduced for frequencies above 0.4 Hz range, up to about 30 seconds before apnea event. Therefore, for this particular patient, the relative power spectral density at about 0.4 Hz, or another suitable frequency, of the current impedance data versus the baseline pressure data can be compared to a threshold and when the relative power spectral density is below the threshold it is indicative that a sleep apnea event is likely to be imminent. This was also seen in other patients in the study and may be used for this patient population but in alternative embodiments different frequencies at which to determine the power spectral density may be used as well as different thresholds for different patient populations (e.g., based on at least one of age, sex, type of respiratory condition and severity of respiratory condition). In another alternative embodiment, the frequency at which the power spectral density measurement is made as well as the threshold value may be personalized on a patient by patient basis for improved performance. Accordingly, in at least one embodiment, the physiological respiratory signal is impedance (of the patient's respiratory system) and the property is power spectral density of the impedance. A respiratory index value can be determined from the relative power spectral density of the impedance. It can be seen that the relative power spectral density at about 0.4 Hz of the current reactance data versus the baseline pressure data is below a threshold at about 40 seconds before the sleep apnea event.

In all of the examples given above, the relative power densities are determined for certain data over time windows of about 0.1 to about 60 seconds. The longer time windows are useful for cases where the data is more noisy. A time varying index $K_3(t)$ is then determined based on the relative power spectral density at act 608 and then at act 610 the index $K_3(t)$ is compared to a threshold $Th_3$. The value of the threshold $Th_3$ can be obtained as described previously for the other methods 300 and 400 using a table of values from various populations of subjects and finding the threshold for the population of subjects that corresponds to the user. If the comparison indicates that it is not likely that there will be an imminent respiratory failure event then the method 600 proceeds to act 612 where the operating parameters of the breathing assistance device 202 are left the same. Otherwise if the comparison indicates that it is likely that there will be an imminent respiratory failure event then the method 600 proceeds to act 614 where the operating parameters of the breathing assistance device 202 are adjusted (as explained previously) to avoid or reduce the likelihood that the respiratory failure will occur.

It should be noted that at act 608 where the power spectral density is determined, this can be done in a variety of ways. For example, the Welch method, may be used to decompose the power spectral density of the recorded signals. As described, comparing the power spectral density at time points that are distant from a respiratory failure versus time points that imminently precede the respiratory failure event, the power of some frequency components consistently decreases about 30 seconds before the respiratory failure event takes place.

As another embodiment, the Fast Fourier transform can be used to obtain the power spectral density values. Alternatively, a Constant-Q transform may be used which may be advantageous since the power of the recorded data tapers off approximately following a 1/f scaling law and thus absolute power is considerably much lower at higher frequencies, making relative changes in power highly variable. Using a parameterization which is logarithmic in frequency, such as the Constant-Q transform, may provide more stable power estimates, since power will be logarithmically spaced (instead of linearly spaced, as per the FFT method).

It should also be noted that in an alternative embodiment the method 600 of FIG. 8, can be modified such that the indices are determined using at least two of the physiological respiratory signals described with respect to FIGS. 9 to 14 and these indices can be combined and compared to a threshold to predict the imminent occurrence of a respiratory failure event. This may be useful in reducing the number of false positives and false negatives that occur during use.

It should be noted that in the various detection and prediction methods described herein that other weighted measures can be used based on the XX, $R_{var}$, $X_{var}$, $XX_{var}$ and $Ph_B$ signals for each monitoring time period and that $Z_{var,w}$, $Z_{ref,w}$, $XX_{var,w}$, $XX_{ref,w}$ and $Ph_C$ are given as examples. Therefore, the measures of baseline weighted impedance and current weighted impedance may be more generally referred to as a baseline weighted respiratory status value and a current weighted respiratory status value that are each determined using $X_{var}$ and $R_{var}$ over a corresponding monitoring time period.

The preceding paragraphs illustrate the advantages of the described embodiments according to the teachings herein since they are able to fill a gap in current breathing assistance devices where there is a lack of continuous information about whether the user is experiencing respiratory failure or is predicted to soon experience respiratory failure. While the prediction method uses additional physiological signals, these signals may not be too difficult to obtain if the user is staying at a medical facility for an expanded period of time.

In another aspect it may be appreciated that a further advantage of having a breathing assistance device controller that is small in size and is light weight is that it is adaptable for use with any breathing assistance devices by using different tube adapters. While the use of different tube adaptors may also require compensation for tubing resistance, in at least some embodiments, the actuator 216 can be kept out of the main tubing path, so that it that does not add any extra resistance to the tubing (e.g. <0.6 cmH$_2$O/L/s).

In another aspect, at least one of the embodiments of the breathing assistance device controller and/or systems described herein that utilize the controller may be further simplified by operating at a single frequency. Although known single frequency FOT machines commonly operate at a frequency close to breathing (e.g. 4-5 Hz), the various embodiments described herein can operate at a higher frequency which allows for the use of a smaller, lighter actuator 216, that enables the breathing assistance device controller to have lower power consumption, more precise signal processing and a smaller footprint so that it can more easily be used with existing breathing assistance devices in an inline fashion. This is because higher frequencies are not contaminated as much by breathing noise which leads to higher Signal to Noise Ratio (SNR). Consequently, the required amplitude of oscillation of the air pressure perturbation that is sent to the user becomes smaller and may be provided by an actuator that is smaller and lighter and perhaps cheaper. Furthermore, using a higher frequency of oscillation also reduces the discomfort that the user (e.g. patient) receives from sensing vibrations in the airflow that is provided to them.

In another aspect, any of the embodiments described herein can be modified for using the breathing assistance device controller 202 to compensate for any leakage around the perimeter of the mask where the mask meets the face and/or nose of the user. For example, mask leakage can be detected by either any of the breathing assistance device controllers or the breathing devices described herein and then the breathing assistance device controller can adjust a control signal provided to the breathing device to increase the pressure in the air flow that is provided to the user to compensate for the air leakage.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

The invention claimed is:

1. A controller for controlling the operation of a breathing assistance device that provides breathing assistance to a user, wherein the controller comprises:
a processor that is electronically coupled to one or more sensors to receive sensor data and Polysomnography (PSG) data, the processor being configured to measure at least one airflow parameter of the user's airflow from the sensor data and at least one PSG parameter of the user from the PSG data and to generate a control signal for the breathing assistance device for a current monitoring time period by:
generating a respiratory index value that is determined during the current monitoring time period to predict a respiratory failure for the user by:
determining a current weighted respiratory status value based on weighting a reactance and a resistance for the user's respiratory system determined from the measured airflow parameters for the current monitoring time period to generate a first index value; generating a second index value that is determined from at least one PSG signal for the current monitoring time period; and generating the respiratory index value from the first and second index values;
updating the control signal when a comparison of the respiratory index value to a threshold value indicates that the respiratory failure is detected or is predicted to occur and otherwise maintaining the control signal at a previous setting; and
sending the control signal to the breathing assistance device to adjust the operation of the breathing assistance device during use.

2. The controller of claim 1, wherein the processor is electronically coupled to at least one polysomnography (PSG) sensor that measures the at least one PSG signal from the user and the at least one PSG sensor comprises at least one sensor for obtaining PSG data used to measure EEG, EOG, EMG, respiratory CO2, O2, some other gas in the user's expired breath or any combination thereof.

3. The controller of claim 1, wherein the breathing assistance device is any type of invasive or a Non-Invasive Ventilation (NIV) device comprising an anesthesia machine, an oxygenator of COPD, an ICU ventilator, a home ventilator, a mechanical ventilator, a continuous positive airway pressure (CPAP) device, a BiPAP device, an APAP device and a PAP device.

4. A controller for controlling the operation of a breathing assistance device that provides breathing assistance to a user, wherein the controller comprises:
a processor that is electronically coupled to one or more sensors to receive sensor data, the processor being configured to direct the one or more sensors to measure the at least one airflow parameter of the user's air flow from the sensor data and to generate a control signal for the breathing assistance device for a current monitoring time period by:
generating a respiratory index value that is determined during the current monitoring time period to predict a respiratory failure for the user by:
determining the respiratory index value based on a peak of a relative power spectral density between a current time period and a baseline period for a physiological respiratory signal;
updating the control signal when a comparison of the respiratory index value to a threshold value indicates that the respiratory failure is likely to occur within a predicted time period and otherwise maintaining the control signal at a previous setting; and
sending the control signal to the breathing assistance device to adjust the operation of the breathing assistance device during use.

5. The controller of claim 4, wherein the physiological respiratory signal is one of a flow rate of the air provided to the user, a pressure of the air provided to the user, a tidal volume of air inspired by the user, and a resistance of the user's respiratory system.

6. The controller of claim 4, wherein the physiological respiratory signal is a flow rate for the air provided to the user and the relative power spectral density is determined for a frequency range less than about 0.2 Hz or greater than about 2 Hz.

7. The controller of claim 4, wherein the physiological respiratory signal is a pressure for the air provided to the user and the relative power spectral density is determined for a frequency range less than about 0.2 Hz or greater than about 2 Hz.

8. The controller of claim 4, wherein the physiological respiratory signal is a tidal volume of air inspired by the user and the relative power spectral density is determined for a frequency range of about 0 Hz to 0.9 Hz.

9. The controller of claim 4, wherein the physiological respiratory signal is a resistance of the user's respiratory system and the relative power spectral density is determined for a frequency range greater than about 0.4 Hz and preferably 0.5 Hz.

10. The controller of claim 4, wherein the physiological respiratory signal is a reactance of the user's respiratory system and the relative power spectral density is determined for a frequency range of about 0.3 Hz to 0.6 Hz.

11. The controller of claim 4, wherein the physiological respiratory signal is an impedance of the user's respiratory system and the relative power spectral density is determined for a frequency of about 0.4 Hz.

12. The controller of claim 4, wherein the current time period ranges up to about 60 to 120 seconds, and the baseline period ranges from about 120 to 300 seconds before a respiratory failure event.

13. The controller of claim 4, wherein the predicted time period is about 0.1 to 120 seconds.

14. The controller of claim 4, wherein the breathing assistance device is any type of invasive or a Non-Invasive Ventilation (NIV) device comprising an anesthesia machine, an oxygenator of COPD, an ICU ventilator, a home ventilator, a mechanical ventilator, a continuous positive airway pressure (CPAP) device, a BiPAP device, an APAP device and a PAP device.

15. A controller for controlling the operation of a breathing assistance device that provides breathing assistance to a user, wherein the controller comprises:
a processor that is electronically coupled to one or more sensors to receive sensor data therefrom, the processor being configured to perform measurements using the sensor data to measure at least one airflow parameter of the user's airflow and to generate a control signal for the breathing assistance device for a current monitoring time period by:

generating a respiratory index value that is determined during the current monitoring time period to predict a respiratory failure for the user by:
performing a Forced Oscillation Technique (FOT) on the user to determine at least one of a reactance, resistance and an impedance of the user's respiratory system; and
generate the respiratory index value based on a peak of a relative power spectral density between a current time period and a baseline period for a physiological respiratory signal including at least one of the reactance, resistance and an impedance of the user's respiratory system;
updating the control signal when a comparison of the respiratory index value to a threshold value indicates that the respiratory failure is likely to occur within a predicted time period and otherwise maintaining the control signal at a previous setting; and
sending the control signal to the breathing assistance device to adjust the operation of the breathing assistance device during use.

16. The controller of claim 15, wherein the controller is configured to actuate a pressure generator to generate an airway pressure perturbation that is superimposed on the airflow that is provided to the user and the airway pressure perturbation is generated to have at least one frequency.

17. The controller of claim 16, wherein the at least one frequency is in the range of 0.001 Hz to 100 THz.

18. The controller of claim 16, wherein the at least one frequency is at about 37 Hz or at about 79 Hz and the airway pressure perturbation is about 0.1 cmH2O.

19. The controller of claim 15, wherein the predicted time period is about 0.1 to 120 seconds.

20. A controller for controlling the operation of a breathing assistance device that provides breathing assistance to a user, wherein the controller comprises:
a processor that is electronically coupled to one or more sensors to receive sensor data, the processor being configured to perform measurements of at least one airflow parameter from the sensor data and to generate a control signal for the breathing assistance device for a current monitoring time period by:
generating a respiratory index value that is determined during the current monitoring time period to detect a respiratory failure for the user by:
determining a current weighted respiratory status value based on weighting a reactance and a resistance for the user's respiratory system determined from the measured airflow parameters for the current monitoring time period; and
generating the respiratory index value based on a deviation of the current weighted respiratory status value from a baseline weighted respiratory status value;
updating the control signal when a comparison of the respiratory index value to a threshold value indicates that the respiratory failure is detected to occur and otherwise maintaining the control signal at a previous setting; and
sending the control signal to the breathing assistance device to adjust the operation of the breathing assistance device during use.

21. The controller of claim 20, wherein the sensor data for measuring at least one airflow parameter of the user's airflow is based on measuring pressure and/or airflow rate of the air provided to the user from the breathing assistance device.

22. The controller of claim 20, wherein the baseline weighted respiratory status value is determined from measurements obtained from the user during an initial monitoring period when the user first starts using the breathing assistance device or during a healthy breathing period without any respiratory failure events when the user is using the breathing assistance device.

23. The controller of claim 20, wherein the baseline weighted respiratory status value is updated periodically from measurements obtained from the user based on a recent monitoring period while the user is using the breathing assistance device.

24. The controller of claim 20, wherein when the user has a chronic respiratory condition the baseline weighted respiratory status value is determined from a population of individuals having a same physical size, age, gender and the chronic respiratory condition compared to the user.

25. The controller of claim 20, wherein when the user has a chronic respiratory condition the baseline weighted respiratory status values is determined from measurements obtained from the user when the user is breathing normally after receiving treatment for the chronic respiratory condition.

26. The controller of claim 20, wherein values for the weights are determined from values in a table of weights that are categorized based on different respiratory conditions and different levels of severity for the respiratory condition for different patient populations.

27. The controller of claim 20, wherein a first weight applied to a reactance value relative is larger or smaller compared to a second weight applied to a resistance value depending on whether the user has a respiratory condition and a severity level of the respiratory condition.

28. The controller of claim 20, wherein the current weighted respiratory status value and the baseline weighted respiratory status value are impedance values determined from FOT measurements.

29. The controller of claim 20, wherein the controller is configured to actuate a pressure generator that is electrically coupled to and controlled by the processor to generate an airway pressure perturbation that is superimposed on the airflow that is provided to the user.

30. The controller of claim 29, wherein the breathing assistance device comprises the actuator or the breathing assistance device controller comprises the actuator.

31. The controller of claim 29, wherein the airway pressure perturbation is generated to have at least one frequency for FOT measurement, and the at least one frequency is in the range of 0.001 Hz to 100 THz.

32. The controller of claim 31, wherein the at least one frequency is at about 37 Hz or about 79 Hz and the airway pressure perturbation is about 0.1 cmH2O.

* * * * *